(12) United States Patent
Contag et al.

(10) Patent No.: US 9,080,977 B2
(45) Date of Patent: Jul. 14, 2015

(54) APPARATUS AND METHODS FOR FLUORESCENCE GUIDED SURGERY

(75) Inventors: Pamela Contag, San Jose, CA (US); Bradley W. Rice, Danville, CA (US)

(73) Assignee: Xenogen Corporation, Alameda, CA (US)

(*) Notice: Subject to any disclaimer, the term of this patent is extended or adjusted under 35 U.S.C. 154(b) by 1330 days.

(21) Appl. No.: 11/877,414

(22) Filed: Oct. 23, 2007

(65) Prior Publication Data

US 2008/0103390 A1    May 1, 2008

Related U.S. Application Data

(60) Provisional application No. 60/853,842, filed on Oct. 23, 2006.

(51) Int. Cl.
*A61B 5/05*    (2006.01)
*G01N 21/64*    (2006.01)
*A61B 19/00*    (2006.01)
(Continued)

(52) U.S. Cl.
CPC ............ *G01N 21/6428* (2013.01); *A61B 19/52* (2013.01); *G01N 21/6456* (2013.01); *A61B 18/20* (2013.01); *A61B 19/5244* (2013.01); *A61B 2017/00057* (2013.01); *A61B 2018/00642* (2013.01); *A61B 2018/00904* (2013.01);
(Continued)

(58) Field of Classification Search
CPC .... A61B 18/20; A61B 19/52; A61B 19/5244; A61B 2017/00057; A61B 2018/00642
USPC .......... 600/407, 427, 476, 477, 478; 356/456, 356/364, 433
See application file for complete search history.

(56) References Cited

U.S. PATENT DOCUMENTS 6,748,259 B1 *    6/2004    Benaron et al. ............... 600/476
2004/0010192 A1    1/2004    Benaron et al.
(Continued)

FOREIGN PATENT DOCUMENTS

WO    WO 2008/020298    3/2008

OTHER PUBLICATIONS

Veiseh et al., "Tumor Paint: A Chlorotoxin:Cy5.5 Bioconjugate for Intraoperative Visualization of Cancer Foci," Cancer Res 2007; 67; (14). Jul. 15, 2007.

(Continued)

*Primary Examiner* — Baisakhi Roy
(74) *Attorney, Agent, or Firm* — Fish & Richardson P.C.

(57) ABSTRACT

Disclosed are apparatus and methods for quantifying fluorescent distribution within a surgery site of a patient in an operating room, wherein the surgery site has been exposed for a surgery procedure. Excitation light is provided at each of a plurality of positions at the surgery site in a method embodiment. The excitation light is significantly more intense than any other light sources that are present in the operating room. Fluorescent emission is detected from the surgery site in response to each of the excitation light positions so as to obtain a fluorescent emission image for each excitation light position. The fluorescent light distribution that is internal to a surface of the surgery site is quantified based on the obtained fluorescent emission images. In one aspect, the quantifying operation includes utilizing a structured light source to form a structured light grid over the surgery site surface to thereby obtain a three dimensional (3D) surface mesh of the surface of the surgery site based on the structured light grid.

21 Claims, 8 Drawing Sheets

(51) Int. Cl.
  *A61B 18/20* (2006.01)
  *A61B 17/00* (2006.01)
  *A61B 18/00* (2006.01)
(52) U.S. Cl.
  CPC . *A61B2019/5231* (2013.01); *A61B 2019/5255* (2013.01); *G01N 2201/1293* (2013.01)

(56) References Cited

U.S. PATENT DOCUMENTS

2004/0073120 A1 4/2004 Motz et al.

2005/0182321 A1 8/2005 Frangioni
2005/0285038 A1 12/2005 Frangioni

OTHER PUBLICATIONS

International Search Report dated Apr. 24, 2008 in PCT Application No. PCT/US2007/082289.
Written Opinion dated Apr. 24, 2008 in PCT Application No. PCT/US2007/082289.

* cited by examiner

APPARATUS AND METHODS FOR FLUORESCENCE GUIDED SURGERY

CROSS-REFERENCE TO RELATED APPLICATIONS

This application claims priority under 35 U.S.C. 119(e) of U.S. Provisional Application No. 60/853,842, filed on 23 Oct. 2006 and titled "Optical Macroscope Fluorescence Guided Surgery," by Pamela R. Contag, which application is herein incorporated by reference in its entirety for all purposes.

BACKGROUND OF THE INVENTION

The present invention relates to imaging technology. In particular, it relates to systems and methods that facilitate the measuring and/or imaging of a fluorescent light source distribution inside a subject.

Imaging with light is steadily gaining popularity in biomedical applications. One currently popular light imaging application involves the capture of low intensity light emitted from a biological subject. This technology is known as in vivo optical imaging. Light emitting probes that are placed inside the subject typically indicate where an activity of interest might be taking place. In one application, cancerous tumor cells are targeted with a fluorescent probe consisting of a fluorescent dye conjugated to a targeting agent such as chlorotoxin.

In surgical applications, such a probe might be injected prior to surgery to help define the location and boundaries of the tumor, to improve resection results. During surgery on particular anatomical area of a subject, the area of interest may be imaged using any number of imaging techniques. One type of imaging is referred to as fluorescence imaging. Photons emitted by labeled cells scatter in the tissue of the subject, resulting in diffusive photon propagation through the tissue. As the photons diffuse, many are absorbed, but a fraction reaches the surface of the subject. The photons emitted from surface of the subject can then be detected by a camera. Light imaging systems capture images that record the two-dimensional (2D) spatial distribution of the photons emitted from the surface. This 2D spatial distribution of the photon can be analyzed to provide information regarding the target cells.

It would be beneficial to provide improved apparatus and methods for fluorescent imaging during surgery.

SUMMARY OF THE INVENTION

Accordingly, apparatus and methods for quantifying fluorescent distribution within a surgery site of a patient in an operating room, wherein the surgery site has been exposed for a surgery procedure, are provided. Excitation light is provided at each of a plurality of positions at the surgery site in a method embodiment. The excitation light is significantly more intense than any other light sources that are present in the operating room. Fluorescent emission is detected from the surgery site in response to each of the excitation light positions so as to obtain a fluorescent emission image for each excitation light position. The fluorescent light distribution that is internal to a surface of the surgery site is quantified based on the obtained fluorescent emission images.

In a specific implementation, the provided excitation light is pulsed, and the detecting of fluorescent emission is synchronized with the pulsed excitation light. The pulsing and detecting operations result in a substantial reduction or elimination from the quantification operation of any effect from any other light sources in the operating room. In another embodiment, the quantifying operation includes utilizing a structured light source to form a structured light grid over the surgery site surface to thereby obtain a three dimensional (3D) surface mesh of the surface of the surgery site based on the structured light grid. In a further aspect, a photographic image of the surgery site and/or an image of the structured light grid is obtained. An image of the quantified fluorescent light distribution is overlaid with the photographic image and/or a three dimensional (3D) surface mesh obtained from the structured light grid image so as to form an overlay image. The overlay image is presented in a display. In a further aspect, the 3D surface mesh is registered with one or more other 3D image that were obtained with another imaging modality so that the 3D surface mesh of the presented overlay image can be used together with the co-registered one or more other 3D images. In yet another embodiment, the operations of providing excitation light, detecting, and quantifying are repeated for a plurality of wavelengths of the excitation light. An autofluorescent spectra and a fluorescent spectra of one or more fluorescent probes are unmixed from the detected fluorescent emission. The one or more probes can take the form of an exogenous probe injected into the surgery site prior surgery and/or an endogenous autofluorescent spectral signature that is unique to a given cancer cell of the surgery site.

In another embodiment, the excitation light is provided in a steady state and the other lights of the operating room have a different spectrum than the one or more fluorescent probes so that the operating room lights are unmixed from the fluorescent probes so as to substantially minimize the effect of the operating room lights on the detected fluorescent emission.

In another aspect, the quantification operation is performed during a surgical procedure so that the fluorescent light distribution is quantified for at least a deep tissue portion of the surgery site, whereby the quantification operation is based on a photon diffusion model and a diffuse tomography algorithm. In another implementation, excitation light is provided sequentially at each of a plurality of positions, and each position is on a side of an object of interest that differs from a side from which the fluorescent emission is detected. In a further aspect, excitation light is provided at least to one position that is on a same surface from which the fluorescent emission is detected. In another further aspect, at least one excitation light position is internal to the surface of the surgery site.

In an alternative embodiment, the invention pertains to an imaging apparatus for quantifying fluorescent distribution in patient in an operating room, wherein the patient has a prepared surgery site that has been exposed for a surgery procedure. The apparatus includes one or more excitation light sources for providing excitation light, wherein the excitation light is significantly more intense than any other light source that is present in the operating room. The apparatus further includes one or more optical elements for providing excitation light from the one or more excitation light sources to a plurality of positions at the surgery site and a fluorescence imager for detecting fluorescent emission from the surgery site in response to the pulsed excitation light provided to the positions at the surgery site. The apparatus also has a controller a controller configured to perform one or more of the above described operations. For instance, the controller is configured to: (i) cause at least one excitation light source to provide excitation light and cause the one or more optical elements to provide pulsed excitation light to each of the plurality of positions at the surgery site, and (ii) quantify the fluorescent light distribution that is internal to a surface of the surgery site based on the detected fluorescent emission.

In a specific embodiment, the excitation light source provides pulsed light and the controller is further configured to synchronize the pulsing of the excitation light with the detecting of the fluorescent emission. In this aspect, the apparatus also has a photographic imager for imaging light from the surgery site and a display, and the controller is further configured to gate the photographic imager so as to obtain a photographic image of the surgery site during a time period when the excitation light is not being pulsed and overlay an image of the quantified fluorescent light distribution with the photographic image so as to form an overlay image. The controller is also configured to present the overlay image in the display. In another aspect, the apparatus also includes a structured light source for forming a structured light grid over the surgery site, and the controller is further configured to cause the structured light source to form the structured light grid over the surgery site surface. In this embodiment, the controller is also configured to gate the photographic imager so as to obtain a photographic image of the structured light grid over the surgery site during a time period when the excitation light is not being pulsed, obtain a three dimensional (3D) surface topography mesh based on the structured light image, and overlay an image of the quantified fluorescent light distribution with the 3D surface topography mesh so as to form an overlay image. The controller is then configured to present the overlay image in a display.

In a further embodiment, the apparatus includes a first filter for receiving the excitation light and selecting one or more wavelengths for the excitation light and a second filter for receiving the fluorescent emission and selecting one or more wavelengths for the emission. The controller is configured to repeat the operations of causing the excitation light, synchronizing, and quantifying for a plurality of wavelengths of the excitation light selected with the first or second filter and unmixing an autofluorescent spectra and a fluorescent spectra of one or more fluorescent probes from the detected fluorescent emission, wherein the one or more probes include one or more of the following: an exogeneous probe injected into the surgery site prior surgery and/or an endogenous autofluorescent spectral signature that is unique to a given cancer cell of the surgery site.

In yet another embodiment, the provided excitation light is provided in a steady state and the other lights of the operating room have a different spectrum than the one or more fluorescent probes so that the operating room lights are unmixed from the fluorescent probes so as to substantially minimize the effect of the operating room lights on the detected fluorescent emission. In another aspect, the one or more optical elements for providing excitation light to the plurality of positions at the surgery site are in the form of a plurality of optical fibers. In a further aspect, an end of each fiber is arranged in a ring that is placeable around a perimeter of the surgery site so that the fiber ends are distributed around the ring. In yet another aspect, a first end of each fiber is coupled to one of the pulsed excitation light sources and a second end of each fiber that is opposite the first end is placeable at one of the positions of the surgery site, wherein the controller is configured to turn on each excitation light source at each first fiber end so that the surgery site position sequentially receives excitation light. Alternatively, the one or more excitation light sources are movable, wherein the controller is configured to move the one or more excitation light sources so that each fiber is sequentially coupled to one of the excitation light sources that is turned on by the controller and such that that the surgery site positions sequentially receive excitation light from a second end of each fiber that is opposite the first end. In yet another embodiment, the apparatus includes a near infrared filter for passing only fluorescent emission to the fluorescence imager, wherein the fluorescence imager is a near infrared detector.

In another embodiment, the invention pertains to at least one computer readable storage medium having computer program instructions stored thereon that are arranged to perform one or more of the above described operations.

These and other features of the present invention will be presented in more detail in the following specification of the invention and the accompanying figures, which illustrate by way of example the principles of the invention.

DETAILED DESCRIPTION OF THE SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

In general, apparatus and techniques for quantifying fluorescence emission from a subject in operating room lighting conditions, e.g., during surgery, are provided. Mechanisms for accounting for the ambient and/or operating room light during the fluorescence quantification are implemented.

Mechanisms for using a structured light source in conjunction with multiple excitation light sources provided sequentially to the surgical site to obtain three-dimensional (3D) surface topography and perform 3D fluorescence reconstruction are also provided. Mechanisms for overlaying a fluorescence image obtained from the subject over a photographic image and/or a 3D surface mesh of such subject may also be provided.

The combination of structured light imaging and fluorescence imaging allows both a three dimensional, substantially real time, image of the tissue identified by a fluorescent functional probe (e.g., as diseased or normal based the fluorescent functional probe) and a reference back to the actual patient tissue by the presence of a light guide or photographic image directly illuminating the object of interest (and visualized by the surgeon) in the surgical field.

Figure 1:
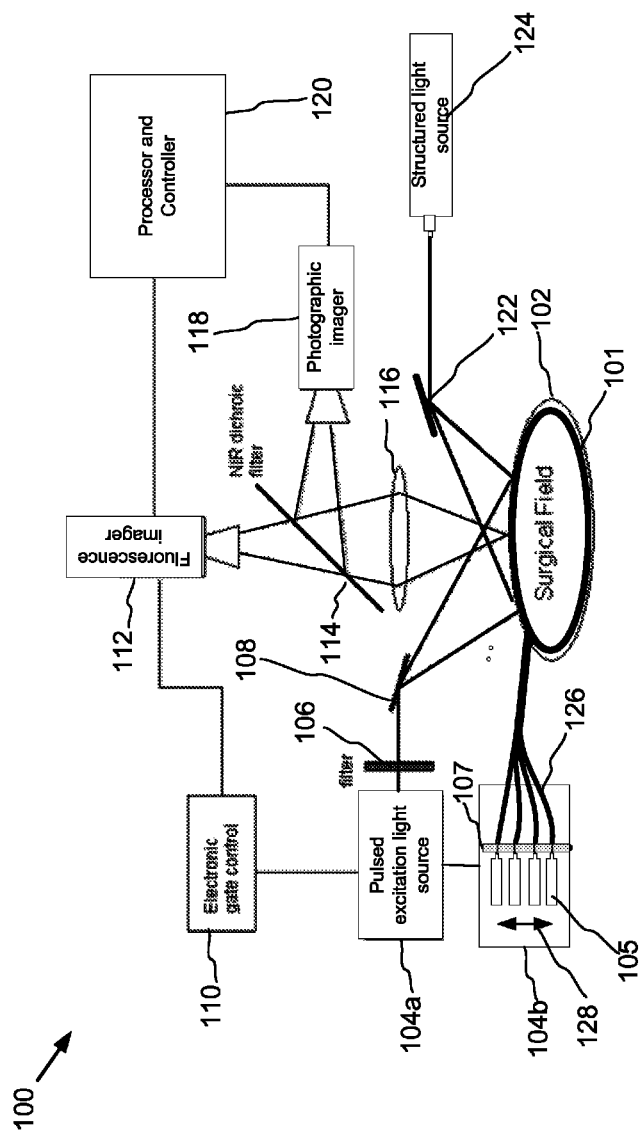
FIG. 1 is a diagrammatic representation of a fluorescence quantification and photographic system in accordance with one embodiment of the present invention.

FIG. 1 is a diagrammatic representation of a fluorescence quantification and photographic system 100 in accordance with one embodiment of the present invention. As shown, the system 100 can be used to analyze and image a surgery field 102 of a subject (not shown) under surgical lighting conditions. That is, this system is configured to be used in an operating room before, during, or after surgery. Any mechanism may be utilized to substantially reduce or eliminate the effect of ambient or any other light that is detected during fluorescent emission detection. The illustrated system 100 can include one or more pulsed excitation light sources 104, e.g., each in the form of a pulsed white light source or pulsed laser source. Each pulsed excitation source emits a pulsed excitation light beam that has a high intensity as compared to room light (e.g., white light). Preferably, the peak light intensity of the pulsed light source is 10 to $10^4$ times brighter than the room light.

Trans-illumination and/or epi-illumination may be used. Trans-illumination provides light from the side, or below, the subject or the imaged object of interest that is different than the side of the camera (e.g., incident light from the side of the object of interest and a camera above the object of interest), so that the light travels through the subject. This arrangement provides lower levels of autofluorescence, which is useful for 3D tomographic reconstructions. Also, the ability to selectively position a transillumination point relative to a fluorescent probe fixed within the subject, provide additional information that can be used for 3D tomographic reconstructions. In the illustrated implementation of transillumination, the excitation light source 104b is in the form of a plurality of light sources 105 that can be selectably turned on and off and pass through a filter 107, which allows a user to change the spectrum of the incident excitation light.

Each excitation source also passes through a corresponding optical fiber 126. The individual fibers 126 from excitation light sources 105 can be used for trans-illumination so that the incident excitation light for each position is directed towards a side of an object of interest, such as the side of a surface tumor or inserted along the side of a deeper tumor, in the surgical field 102. In one embodiment, the outlet positions of the individual fibers are distributed around a perimeter 101 of the surgical field 102.

In alternative transillumination embodiment, the individual excitation light sources 105 may number less than the optical fibers 126, e.g., there is only a single excitation light source for a plurality of fibers. In such an implementation, the one or more excitation light sources 105 may be moved with respect to the optical fiber ends, e.g., in direction 128, (e.g., by a stepper motor or the like) so as to selectably provide a light source to a particular fiber end. For instance, if a single excitation light source is used, this light source can be sequentially moved to each fiber end so as to sequentially provide excitation light to each of the positions in the surgical area via each fiber 126.

Epi-illumination provides the incident light from the same side of the subject that an image is captured (e.g., incident light from above, and a camera above the subject), and is often referred to as reflection-based fluorescent imaging. FIG. 1 schematically shows epi-illumination in accordance with one embodiment. In this case, excitation light source 104a provides excitation light that is directed through filter 106, which is configurable to pass one or more specific wavelengths, and is directed by one or more optical elements, such as diffuser 108, to a position above the subject for provision towards a top surface of the surgical field 102 on the same side of the subject as camera 112.

Each filter may take any suitable form for selectively transmitting various wavelengths or wavelength ranges. By way of examples, each filter may take the form of an interference type filter, such as a bandpass filter, longpass filter and shortpass filter, or a fast tunable filter such as available from Meadowlark Optics of Frederick, Colo.

Epi-illumination provides a faster survey of the subject, but may be subject to higher levels of autofluorescence. Both trans-illumination and epi-illumination may be used. Epi-illumination provides intense surface illumination and may help constrain volume elements near the camera-facing surface of the subject. For example, the epi-illumination constraints may identify artifact voxels near the top surface in a diffuse tomography reconstruction, which are then removed by software.

One or more output optical elements are arranged to direct the fluorescence emission from the surgical field, which is caused in response to the pulsed excitation light (e.g., from excitation sources of 104a and/or 104b), towards a fluorescence imager 112 for imaging the fluorescence emissions from the surgical field 102. As shown, the output optical elements may include a focusing optical element 116 for directing the fluorescence emission towards fluorescence imager 112 and a filter 114 for passing only the fluorescence emission towards the fluorescence imager 112. In one implementation, the fluorescence imager 112 takes the form of a charged coupled detector (CCD) camera that has high sensitivity in the visible and near-infrared (NIR) part of the spectrum. In a further implementation, the camera is an intensified or electron multiplied CCD camera. By way of example, the filter 114 may take the form of a NIR dichroic filter (as shown).

Imaging may be based on either trans- or epi-illumination images. Imaging may also capture both trans- and epi-illumination images, and combine the data. In each view, the light takes a different path through subject, which provides a different set of input criteria and internal light conditions for tomographic reconstruction calculations.

The system also includes a structured light source 124 and a scanner 122 (e.g., scanning laser galvanometer with mirrors) to generate an adjustable grid whose coordinates can be visualized through projection over the surface of the surgical field and captured by a photographic imager 118 (e.g., a color CCD camera). This adjustable light grid may be used to both map the 3D contour of the surface for the software reconstruction of the 3D image and as a real time guide or contour map (or 3D surface mesh) for a surgeon to navigate a surgical area indicated as diseased by the functional probe as described further below. The photographic imager 118 may also be used to obtain a color image from the surgical field 102. The 3D surface mesh obtained from structured light could also be used to co-register with a 3D anatomical image acquired from an MRI (magnetic resonance imaging) or CT (computerized tomography) imaging system.

One or more controllers and/or processors may be utilized to control the various components of the system 100 and/or analyze/manage fluorescence emission, structured light, and photographic images that are obtained from the subject. As shown, the system 110 includes an electronic gate control 110 for synchronizing the fluorescence imager's detector with the pulsed excitation light source, 104a and/or 104b, so as to reduce the effects of the ambient and/or operation room light. The gate control 110 may also be configured to turn individual light sources 105 on and off or move light sources 105 with respect to corresponding fiber ends for transillumination. The illustrated system 100 also may include a processor and controller 120 for controlling the operation of photographic imager 118 and analyzing/managing images captured by fluorescence imager 112 and photographic imager 118.

The imaging system 100 allows macroscopic visualization before, during, or after surgery. For example, the system 100 may provide visualization on the order of 20-100 μm and is helpful for positioning a surgical instrument at a resolution between the whole body imaging and the microscopic imaging that is currently available for operating room procedures. The lens system may be positioned between the object for view and a camera with a detector size of 0.25 to 1 inch. The lens system may emit minimum fluorescence and may correct for chromatic aberrations in the specified wavelengths of interest. The lenses may be arranged on a movable turret, filter wheel, or other system that allows a working distance close to the object of view for imaging and allows an increased working distance with sufficient room for the surgeon to place manipulation devices and instruments (remote or handheld). The lens system may provide an image quality that is sufficient to differentiate low light level emission from areas in the field of view that are closely associated or side by side.

A difficulty in tomographic imaging of humans (and other types of mammals) is that the complex surface of the subject will change with each subject, and potentially each time the subject is imaged (as its position and body shifts). The probe may also change each time the subject is imaged—in position, size, strength, and spectral distribution. The difficulty, then, is determining the 3D parameters of an internal fluorescent probe distribution, such as the 3D location, size and brightness distribution of a fluorescent probe, given that many parameters needed for tomographic imaging may change with each imaging process.

One distinguishing feature of methods described herein is that they use an actual surface topography of the subject—as it rests under a camera at the time that light images are captured—or any other time. In this case, the methods also employ topographic determination tools. Topographic imaging determines a surface representation of an object, or a portion thereof. In one embodiment, the present invention uses structured light to determine a surface topography for at least a portion of the subject. Tomographic imaging refers to information inside the subject surface. An exemplary illustration of topographic vs. tomographic imaging uses a 2D planar slice through the subject: topography gives the surface (the outer bounding line), while tomography provides information inside the bounding surface.

Another challenge to tomographic reconstruction that is overcome herein: the tissue in subject also autofluorescence. Tissue autofluorescence may act as a source of background or noise to tomographic imaging of a fluorescent probe distribution, and techniques described below also a) model or unmix autofluorescence and b) separate the contributions of tissue autofluorescence from light emitted from the subject surface. This isolates light emitted from the subject surface that corresponds to fluorescent probe.

The present invention overcomes these difficulties and permits real-time fluorescent tomographic imaging, despite variability and complexity of the subject surface, the effects of autofluorescence, or internal fluorescent probe distribution.

The term "fluorescent probe" generally refers to any object or molecule that produces fluorescent light. The fluorescent probe absorbs incident energy of a certain wavelength or wavelength range and, in response, emits light energy at a different wavelength or wavelength range. The absorption of light is often referred to as the "excitation", while the emission of longer wave lights as the "emission". The output wavelength range is referred to herein as 'output spectrum'. The fluorescent probe may include one or more fluorescent light emitting molecules, called 'fluorophores'. A fluorophore refers to a molecule or a functional group in a molecule that absorbs energy of a specific wavelength and re-emits energy at a different wavelength. Many commercially available fluorophores are suitable for use with subject. Suitable fluorophores include Qdot® 605, Qdot® 800, AlexaFluor® 680 and AlexaFluor® 750 as provided by Invitrogen of San Diego, Calif. Both organic and inorganic substances can exhibit fluorescent properties, and are suitable for use with a fluorescent probe. In one embodiment, a fluorescent probe emits light in the range of about 400 nanometers to about 1300 nanometers.

Toward the goal of developing an optical imaging contrast agent that will enable surgeons to intraoperatively distinguish cancer foci from adjacent normal tissue, James M. Olson at the University of Washington Fred Hutchinson Cancer Center developed a chlorotoxin:Cy5.5 (CTX:Cy5.5) bioconjugate that emits near infrared fluorescence signal. Several embodiments of such probe are described in the article by James M. Olson et al., entitled "Tumor Paint: A Chlorotoxin:Cy5.5 Bioconjugate for Intraoperative Visualization of Cancer Foci", American Association for Cancer Research 2007; 67: (14). Jul. 15, 2007, which article is incorporated herein by reference. The probe delineates malignant glioma, medulloblastoma, prostate cancer, intestinal cancer, and sarcoma from adjacent non-neoplastic tissue in mouse models. Preliminary studies also demonstrate that CTX:Cy5.5 can bind specifically malignant cells with high specificity. This probe is suitable for use herein.

The CTX:Cy5.5 probe is synthesized using a mixture of CTX (Alomone Labs, Israel, 250 ul of 2 mg/ml in 50 mM bicarbonate buffer, pH 8.5) and Cy5.5-NHS ester (Invitrogen, 43 ul of 10 mg/ml in anhydrous dimethyl formamide). Conjugation is performed in dark at room temperature for about 1 hour. Unconjugated dye is removed by dialysis against PBS (3 times) using Slide-A-Lyzer (Pierce Biotechnology, IL) membrane (Mr, cutoff, 3500) for 9-18 hours at 4° C. Samples are then diluted with PBS to produce 1, 10, and 20 μM of CTX solution and filtered with a 0.2 μm syringe filter before use. Batches are evaluated by mass spectroscopy and Xenogen IVIS-100 to ensure quality and functionality, available from Caliper Life Sciences, Inc. of Hopkinton, Mass.

Mammals having a fluorescent probe distribution may include mammals such as a human, a small mammal such as a subject, cat, primate, dog, rat or other rodent. Other animals may include birds, zebra-fish, mosquitoes and fruit flies, for example. Other objects and samples are also suitable for use herein, such as eggs and plants. For ease of discussion, the remaining disclosure will show and describe a subject as an imaging object that contains a fluorescent probe.

In one embodiment, simplifying approximations to a photon diffusion model are implemented in order to expedite the computation time required to perform a reconstruction of the light corresponding to fluorescent probe. With the approximations described below, reconstruction times of less than 5 minutes may be achieved—compared with hours or days for methods that use FEM or Monte Carlo modeling.

Figure 2:
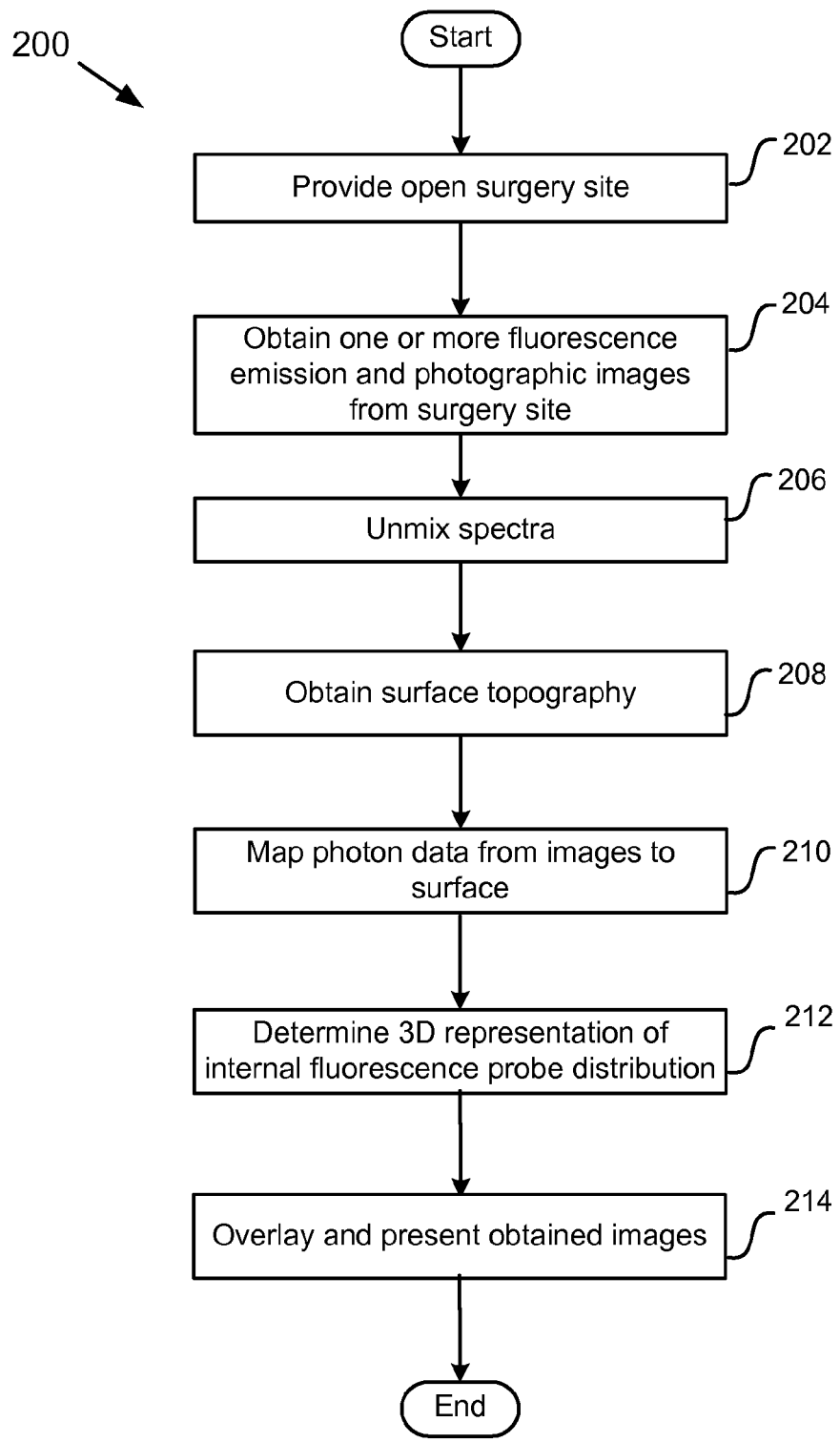
FIG. 2 illustrates a method of obtaining a 3D representation of a fluorescent light distribution located inside a subject in accordance with one embodiment of the present invention.
Figure 3A:
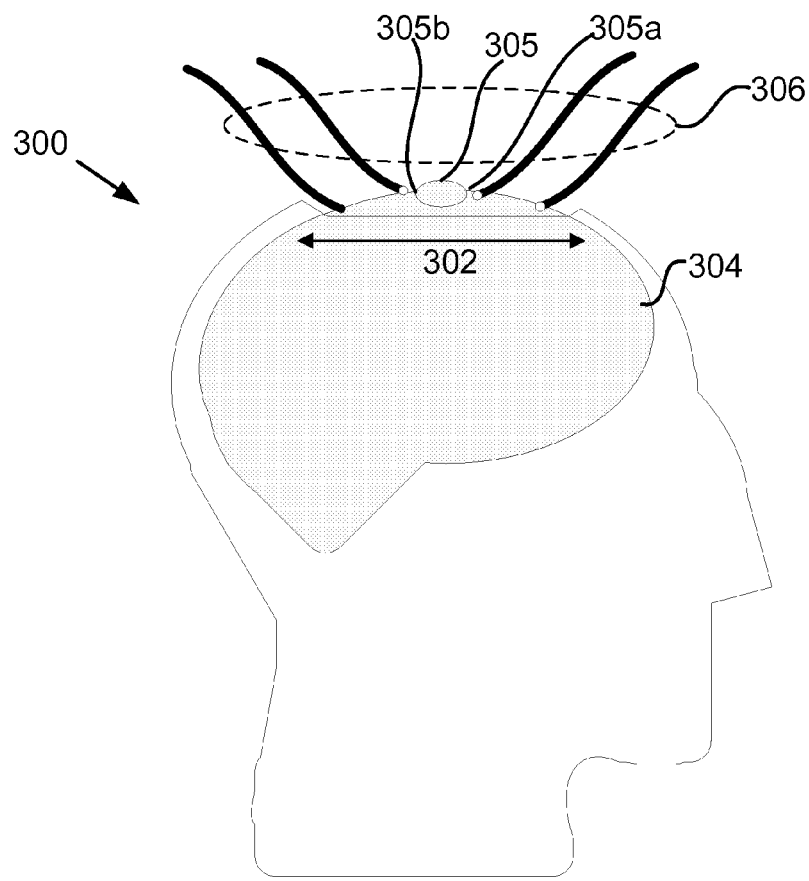
FIG. 3A is a diagrammatic side view of a subject with an exposed brain surgery site from which fluorescent, as well as photographic, images are obtained in accordance with one embodiment of the present invention.

FIG. 2 illustrates a method 200 of obtaining a 3D representation of a fluorescent light distribution located inside a subject in accordance with one embodiment of the present invention. Initially, an open surgery site may be provided in operation 202. In general, the surgery site of the subject will be prepared for surgery by being open so that the initial area of interest is exposed or uncovered. In one example, the brain of the subject may have been imaged prior to surgery to provide a location of a tumor growth. FIG. 3A is a diagrammatic side view of a subject's head 300 that has a portion of the skull removed so as to expose surgery site 302 of the subject's brain 304. Other surgery sites on other areas of the body may require cutting through any number and type of tissues (e.g., such as skin, muscle, fat, organs, etc.) and/or bone to expose an area for a surgical procedure, such as tumor removal.

After a prepared surgery site is provided, one or more fluorescent emission and photographic images of at least a portion of the surgery site may then be obtained in operation 204. The images include fluorescent image data that describes fluorescent light emitted from the subject. The fluorescent image data describes light that falls upon a camera or other photon detector that is distant from the subject. In this case, the fluorescent image data is stored in the images in two-dimensions (2D).

In a transillumination embodiment, intense excitation light point sources are applied sequentially to a plurality of positions on or inserted within the tissue of the surgery site of the subject while fluorescent image data is detected for each excitation position. The object of interest, from which fluorescent emission is captured, may be near the surface of the surgery site or deep within a tissue of the surgery site. In the illustrated example of FIG. 3A, the object of interest 305 is near the surface. A plurality of optical fibers 306 may be applied to a plurality of positions on the surgery site 302 of the exposed brain of the subject 300.

Each fiber 306 may either be inserted into the brain or be placed directly on the brain surface so that the excitation light is directed towards a side of the object of interest that differs from the detector or camera. In the illustrated example, the object of interest is in the form of a tumor growth 305 that rises above the surface of the brain. Since the object of interest 305 is near the surface, the fibers 306 can be placed around object of interest 305 so that excitation light hits the vertical (sloped or straight) sides, e.g., 305a and 305b, of the object. Depending upon the particular tissue's sensitivity to pressure, the tissue can also be compressed down around the object of interest. In the illustrated example, the brain tissue 304 may be pressed around the tumor 305 in an area in which the fibers are placed so that the excitation light hits more of the tumor's sides. Additionally, fibers may be inserted into the tissue of the surgery area 302 so as to have the excitation light hit a side of a deep object of interest or a deeper side of a shallow object of interest or to hit the bottom of any object of interest. That is, a surgical guide wire may be used to guide an optical fiber to the bottom side of the object of interest that is opposite the camera side.

Spectral unmixing may also be performed in operation 206. The spectral unmixing generally separates image data according to spectra from multiple internal fluorescent light sources, including autofluorescence, in an effort to isolate one or more spectra of interest and/or to substantially eliminate autofluorescence. Autofluorescence refers to the natural fluorescence of substances within a material or organism. Human or mammalian tissue has autofluorescence properties that will affect fluorescent imaging. A camera may receive image data that includes both: a) light escaping from the subject surface due to autofluorescence of tissue in the subject, and b) light escaping from the subject surface due to fluorescent probe. From a camera's perspective, these two contributions are often mixed.

The spectral unmixing obtains multiple images, each captured with a different combination of excitation and emission wavelength bands. The spectral unmixing then uses an iterative solution process to separate spectra for multiple internal light sources and/or an autofluorescence internal light source, and outputs a spectrum and/or a spatial distribution map for at least one internal light source. An unmixing process is further described below.

Spectral unmixing may also be used to substantially eliminate the light contributed by the operating room light. In one implementation, the operating room light has a specific spectrum that can be unmixed from the resulting fluorescent emission so as to substantially reduce the effects from the operating room light from the fluorescent results. In this embodiment, a steady state excitation light may be used, as opposed to a pulsed excitation light since the operating room light is reduced via unmixing. Of course, a pulsed excitation source may also be used in conjunction with unmixing the operating room light.

Other techniques besides unmixing may be used to substantially eliminate autofluorescence, such as modeling the contributions of tissue autofluorescence to the light emitted from the subject. Multiple techniques are contemplated for determining autofluorescence and separating it from the surface emission for fluorescent probe or cell. In one embodiment, autofluorescence is determined by measurements made in control subjects (subjects without a fluorescent probe). In this case, an average autofluorescence yield per unit volume of tissue can be derived from images of autofluorescence. The autofluorescence yield can then be used in a forward model of light propagation.

The remaining fluorescent probe emission contributions to the surface emission data can be used for tomographic processing (without the noise and contributions of tissue autofluorescence). The modeled tissue autofluorescence can then be subtracted from the light emitted from the surface, which isolates the light/signal due to the fluorescent probe.

Referring to method 200, the 2D fluorescent image data may then be mapped onto a surface of the surgery site in operation 210. Before the mapping can occur, method 200 obtains a surface representation of at least a portion of the surgery site (208). The surface portion may include all of the surgery site, or a smaller portion. Typically, this portion includes parts of the surgery site that the fluorescent image data will be mapped onto.

The surface representation refers to a mathematical description or approximation of the actual surface of the surgery site, or a portion thereof. The surface representation may be divided into a surface mesh comprising a set of surface elements. In one embodiment, structured light is used to obtain a surface representation of the subject. Structured light uses a set of lines of light that are projected down on the subject at an angle (at about 30 degrees, for example) to the surface normal. The subject generates structured light surface information as each light line reacts to the shape of the subject. Cumulatively, the lines of light each bend or alter in spacing as they pass over the subject. The structured light surface information can be measured by a camera and used to determine the height of the surface at surface portions of the subject that are illuminated by the structured light source. These surface portions are the portions of the subject that face the camera (for a current position of the subject relative to the camera).

A camera captures the structured light surface information, digitizes the information and produces one or more structured light images. A processor, operating from stored instructions, produces a 3D surface representation of the subject—or a portion of the object facing the camera—using the structured light information. More specifically, a processing system, running on stored instructions for generating a topographic representation (a surface map) from the structured light surface information, builds a 3D topographic representation of the subject using the structured light surface information. Structured light image capture, hardware and processing suitable for use with a subject is described further in patent application Ser. No. 11/127,842 and entitled "Structured Light Imaging Apparatus", which is incorporated herein by reference in its entirety.

Figure 3B:
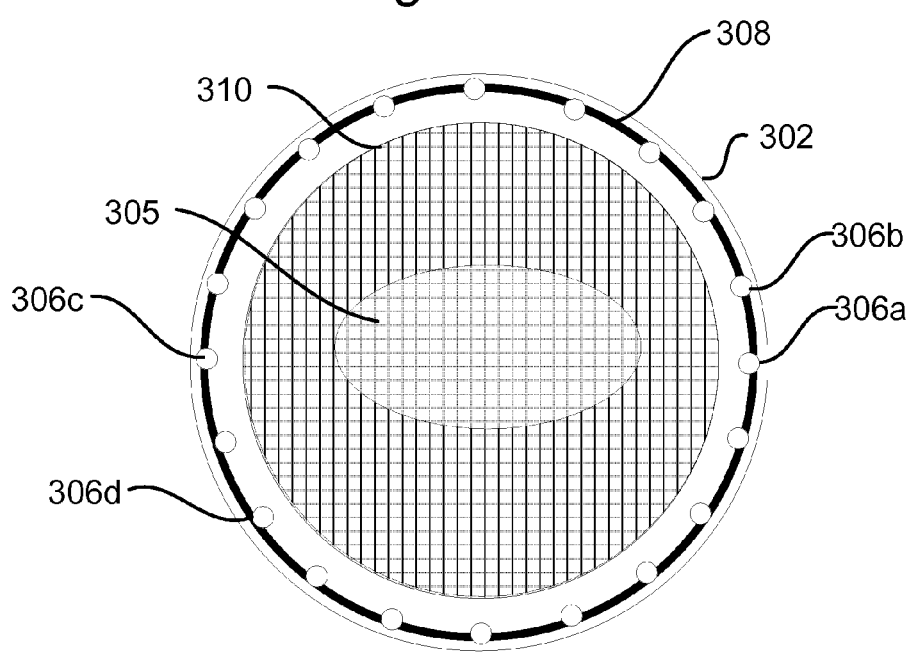
FIG. 3B illustrates a top view of the surgery site of FIG. 3A.

The surface representation need not include the entire surgery site, and may include a portion of the surgery site relevant to a particular imaging scenario. FIG. 3B illustrates a top view of the surgery site 302 and surface tumor 305 of FIG. 3A. As shown, fibers 306 (e.g., 306a-d) are distributed around an outside perimeter or ring 308 of the surgery site 302. The fibers may be coupled together on a sterile ring 308 or any other suitable shape (oval, square, rectangle, polygon, triangle, etc.).

In this example, the surface representation includes an inner structured light area 310 of the surgery site 302 that is sized so as to encompass most of the surgery site, including the object of interest 305, but not the perimeter area covered by the fibers 306. The structured light area 310 is used to determine the surface representation. The placement of the surface representation area with respect to the fibers may be chosen so that the fibers do not adversely affect the structured light area. Alternatively, the surface representation can account for the predefined fiber configuration and eliminate the fiber surfaces from the determined surface representation. Thus, the surface representation is meant to broadly refer to any surface portion of the surgery site and not necessarily the entire surgery site. Typically, the surface representation includes one or more surface elements or regions of interest on the sample that produce surface light emission data related to the internal probe.

Once the surface topography is determined, process flow 200 maps the fluorescent image data in the 2D fluorescent images to fluorescent image data at a surface of the subject (210). This process converts 2D light data collected at a camera to 3D light data at a 3D surface of the subject. In one embodiment, the mapping converts radiance data from the fluorescent images to photon density just inside the surface.

The mapping manipulates 2D camera data according to the geometry between the subject surface and the camera lens to derive values of the light emission intensity (or radiance) at the surface. A variety of techniques can be used to map camera light data to the subject surface. In one embodiment, the mapping uses a simple 3D translation based on the relative position between the camera and subject surface. This permits a 3D translation using the known coordinates from the camera to the subject surface.

Figure 3C:
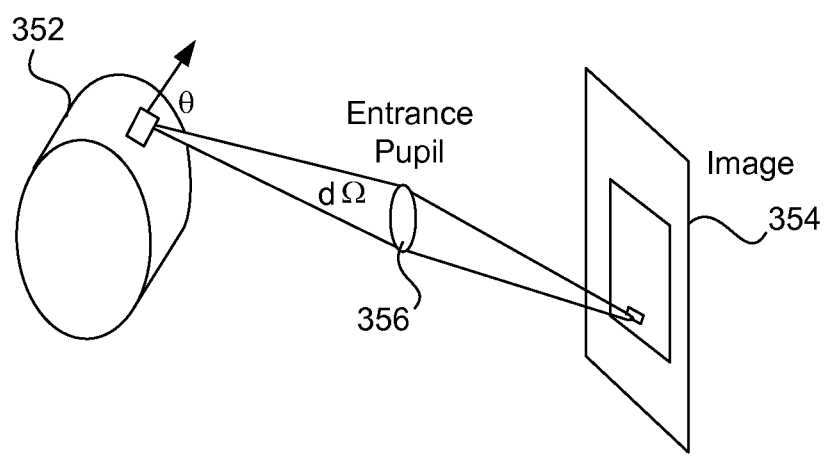
FIG. 3C illustrates a relationship for converting 2D camera data to surface data for a sample surface element.

More sophisticated spatial relationships between a camera and subject may be used. In another embodiment, the angle of the subject surface is also accounted for in the mapping. FIG. 3C illustrates a relationship for converting 2D camera data to surface data for a sample surface element 352. Specifically, FIG. 3C shows a relationship between surface element 352 (on the subject), image 354, and an entrance pupil or camera 356 of an imaging system. Light emitted from surface element 352 passes through entrance pupil 406 and is recorded in image 354. The angle of emission with respect to the surface normal is $\theta$, which is known from the surface topography determined in 208. The entrance pupil 356 subtends a small solid angle $d\Omega$. The imaging system may collect light emitted from surface element 352 on the sample at an angle $\theta$ (measured with respect to the normal to surface element 352) into the solid angle $d\Omega$ subtended by the entrance pupil. This information may then be used to convert image data obtained by the camera into the surface emission intensity corresponding to the surface geometry.

Emission of light from a subject surface may be specified in units of radiance, such as photons/sec/$cm^2$/steradian. In one embodiment, an imaging system captures images of the subject and reports surface intensity in units of radiance. Surface radiance can be converted to photon density just inside the subject surface, using a model for photon propagation at the tissue-air interface, as described below. When the surface representation includes a set of surface elements, the mapping may produce a surface emission data vector that includes photon density at each surface element for the subject topography. The photon density just inside the surface are then related to a light emitting probe distribution inside the subject tissue using a diffusion model.

Method 200 then determines a 3D representation of the internal fluorescent probe distribution to the subject (212). As the term is used herein, a fluorescence probe distribution refers to a description or mathematical depiction of fluorescent light emitters inside the subject. Typically, the fluorescent light corresponds to a fluorescent probe disposed inside the subject. As mentioned above, the fluorescent probe may include a fluorescent marker such as a dye molecule, or a fluorescent reporter that produces fluorescent light based on gene expression.

Light data internal to the subject surface generally refers to mathematical representation or approximation of light within the subject interior. This representation may include a set of points or volume elements, each characterized by 3D position and source strength. In one embodiment, the present invention divides the subject interior into volume elements where each volume element is considered to contain a point light source at its center. A solid mesh of these volume elements then defines a collection of point sources used to approximate light data internal to the subject and the actual probe distribution within subject. For example, a solid mesh of cubic volume elements may be used.

In one embodiment, fluorescent probe includes emits low-intensity light. In one embodiment, a low intensity fluorescent probe of the present invention emits light within subject in the range of about $10^4$ to about $10^{14}$ photons/second, depending on probe concentration and excitation light intensity. For some imaging systems, a fluorescent probe that emits flux in the range of about $10^4$ to about $10^{10}$ photons/second is suitable. Other light fluxes are permissible with the present invention. Photons/second is one unit of measure suitable to quantify the amount of light produced by probe. Other units of measure are known to one of skill in the art, such as Watts. For reference, the conversion of photons/second to Watts is 3.3 nanowatts equals about $10^{10}$ photons/second at 600 nm. In one embodiment, probe emits light between about $10^{-15}$ to $10^{-6}$ watts of light. The amount of light produced by fluorescent probe refers to the light emitted within subject—not necessarily the amount of light generated by an excitation light source (such as an LED) that generates the light incident on the fluorescent probe.

Method 200 uses the fluorescent light emission data from the subject surface, along with tomographic imaging software that models light propagation internal to the subject and solves for fluorescent probe distribution. The internal light propagation modeling includes both a) fluorescent excitation light propagation from the excitation light source, and its entry points into the subject, to the fluorescent probe, and b) fluorescent emission light propagation from the fluorescent probe to the surfaces captured in the fluorescent images.

Tomographic modeling, processing, and fluorescent probe determination of step 212 are described in further detail below. For user convenience, the resultant 3D representation produced by method 200 may be expressed as a pictorial depiction, e.g., on a computer monitor. Thus, the obtained images, e.g., the determined fluorescent probe distribution image and the photographic image (and/or light structure image) may be overlaid and presented in operation 214. Said in another way, an image output to a user may be composed of two or more superimposed parts: a pictorial or surface representation gained from structured and/or photographic light, and a functional image. The structured light source allows determination of a 3D surface topography. Casting fluorescent excitation light onto the specimen permits the acquisition of fluorescence imaging data; an epi-illumination or trans-illumination may be used to generate a reconstructed fluorescence image, which can then be superimposed over a photographic or structured light image of the surface to create an overlay that shows the functional fluorescence image superimposed over a pictorial reference. The coordinates of the functional features can be determined directly from the real time structured light source projected onto the patient's surgical area (e.g., brain) and referred to directly on the real time 3D reconstructed image of the fluorescent source.

The image generated with the above-described system may include a two- or three-dimensional representation of a patient in a macroscopic or microscopic surgical field of view. A computer system and user interface allows a user to readily view and analyze the two- and three-dimensional images and imaging data. The graphics may include, for example, information describing a location and magnitude of electromagnetic radiation located in the field of view.

A graphical user interface may run on one or more processors. The user interface permits the easy use of windows, control icons, and data displayed either in image form or text form. The computer interface may be used for image and data management. In one embodiment, the graphical user interface automatically reconstructs and quantifies light represented on the image. The user interface may include coordinates to orient a user and allow navigation between a three-dimensional representation and an actual image and real time event in the surgical field of view (the patient). The software and user interface may also generate and present the overlay image, which includes the fluorescent image, the photographic image and/or the structured grids with coordinates. In a specific embodiment, the user interface operates via pull down windows for controlling the camera, filters, illumination and illumination source position and data storage and retrieval.

The tomographic imaging is suitable for use with samples having a complex surface, such as a subject. As the term is used herein, a complex surface is any surface that cannot be described solely using a single polygonal description. The reconstruction techniques described herein place no restrictions on the source distribution, such as the number of probes in the sample or the sizes and shapes of the sources, and no restrictions on the geometry, size or shape of the surface.

In some embodiments, method 200 may occur in real time where image capture (204), spectra unmixing (206), topographic acquisition (208) and the data calculations (210-212) all occur without significant delays to a user, e.g., surgeon. In other words, soon after all the images are obtained—e.g., the images are captured or previously captured images are selected and recalled from memory—and the user inputs desired parameters for the tomographic assessment, method 200 outputs 3D details for the internal fluorescent probe. In one embodiment, mapping the fluorescent image data and determining the 3D fluorescent probe distribution finishes in less than about 5 minutes. In another embodiment, details of a fluorescent probe distribution are determined in less than about 1 minute. A video display may then show a pictorial representation of the tomographic reconstruction output on a monitor to a user. This quick processing allows a user to repeat process flow 200—or change parameters in the tomographic assessment relatively easily. This increases efficiency. This real time imaging permits surgeons to assess the fluorescent distribution of the surgical site prior, during, or post surgery.

Figure 4A:
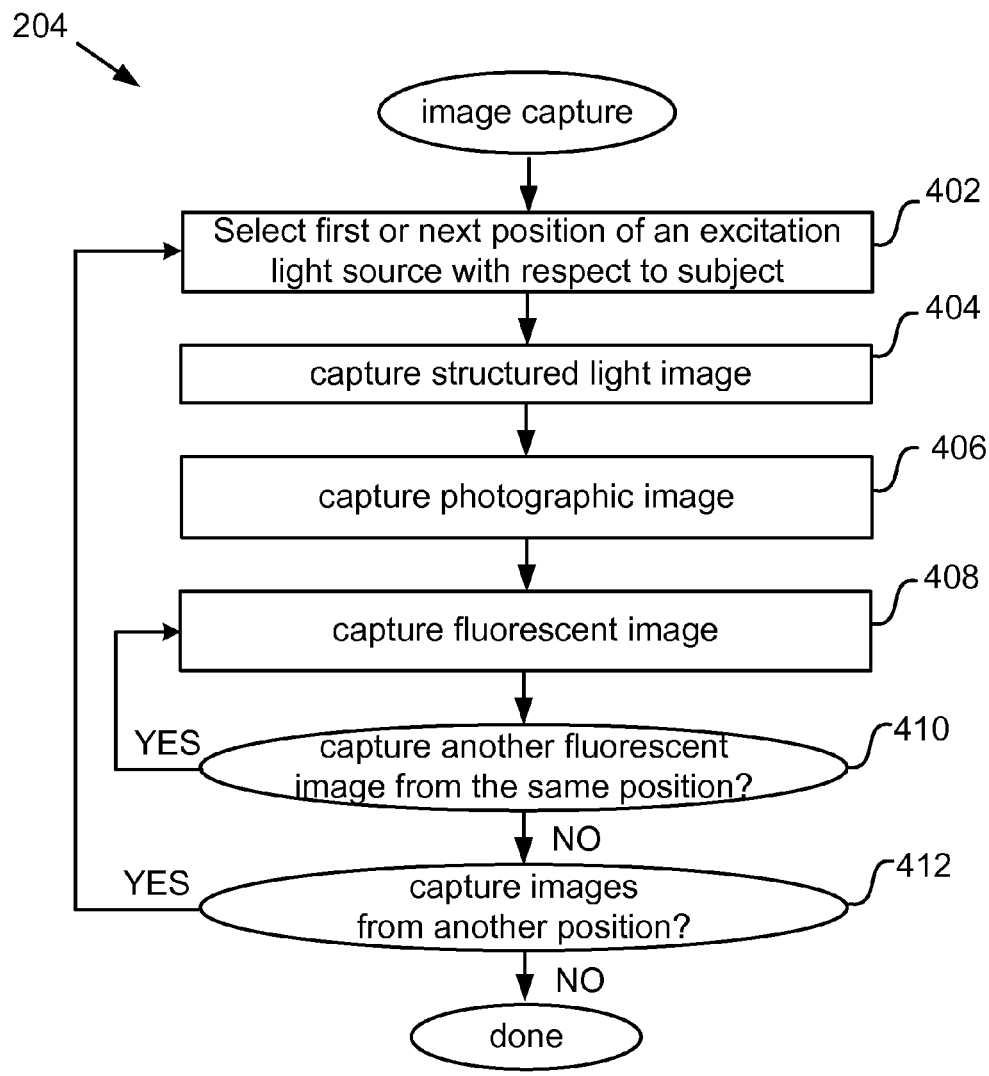
FIG. 4A shows a process flow for fluorescent image capture (of FIG. 2) according to a specific embodiment of the present invention.

FIG. 4A shows a process flow for fluorescent image capture 204 (of FIG. 2) according to a specific embodiment of the present invention. In one embodiment, image capture 204 occurs with the subject resting or lying on a flat surface in a resting position. The subject may be (and is likely) anesthetized.

As shown, image capture 204 begins by selecting a first position of an excitation light source with respect to the subject in operation 402. In the example of FIG. 3B, a first one of the fiber optics, such as 306a, is selected. Alternatively, an epi-excitation source may be selected to be incident on the surgery site. The user may also initiate image capture 204 using a computer associated with the imaging system. In one embodiment, each of the excitation light sources or optic fibers is selectable. In this case, the imaging system selects an optic fiber according to a control signal provided by a computer in the imaging system. For example, a user may input a desired image position via the computer user interface, and the imaging control system selects the light source or fiber accordingly. Alternatively, a desired position for the light source may be pre-programmed based on an automated data collection routine that the user initiates. In either case, the excitation source for the selected fiber may be turned on or an excitation light that is on may be moved to the selected fiber end or a fiber switch (not shown) may selectively switch the excitation light to the selected fiber.

The camera then captures a structured light image (404). Structured light image capture may be accomplished using a structured light projection system. In a specific embodiment, the structured light projection system projects structured light down onto the subject from an angle, and the camera (also above the subject, or on the same side of the subject as the projector) captures the altered structured light. Suitable structured light generation systems are described in commonly owned and patent application Ser. No. 11/127,842. The structured light image data is also transferred to an image processing unit and/or a processor in the imaging system for storage for further processing to build a 3D surface representation.

A camera may also capture a photographic image (406). The photographic image data is transferred to an image processing unit and/or a processor in the imaging system for storage. The photographic image may be subsequently used for display. For example, the photographic image may be used in an overlay image that includes both the photographic image and fluorescent probe distribution (output from 212). The overlay provides a simple pictorial view to facilitate user visualization of the internal fluorescent probe distribution.

The camera also captures a fluorescent light image (408). Fluorescence imaging illuminates the subject to excite fluorescence molecules in the internal fluorescent probe, and then captures an image of the subject, or a portion thereof, as the internal probe fluoresces. Fluorescent image capture provides incident light onto into the surgery site with an illumination source. The incident light should be large enough in magnitude to elicit a fluorescent from the probe under operating room lighting conditions. In response to the incident light, light emits from the "excited" fluorescent probe.

Figure 4B:
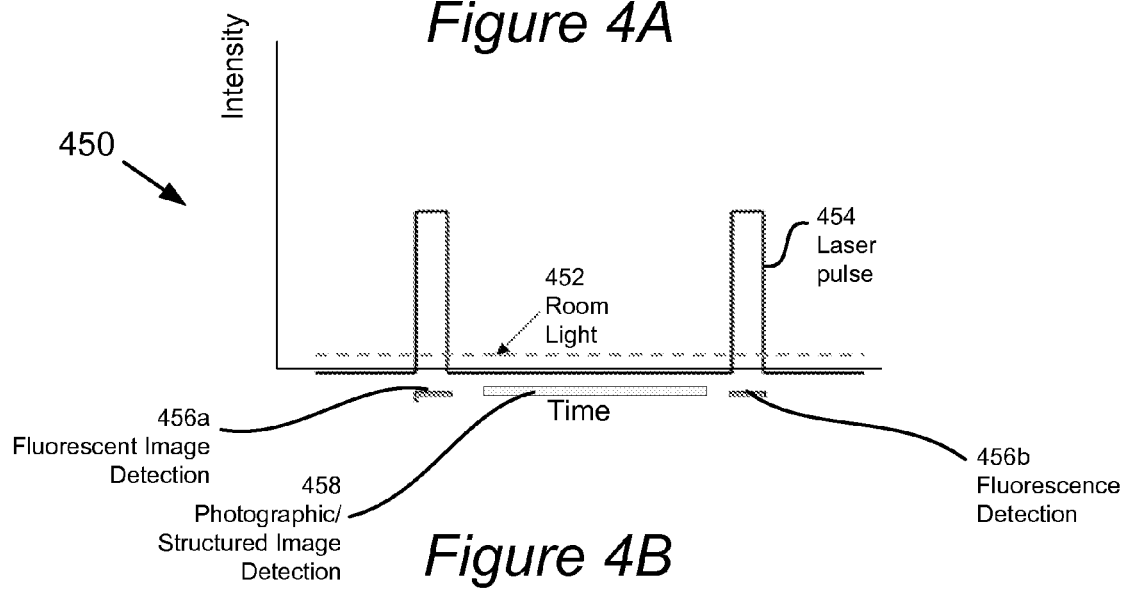
FIG. 4B is a graph of light intensity as a function of time in accordance with one embodiment of the present invention.

The fluorescent excitation is provided by a pulsed intense light source (e.g., 104a or 104b) so as to reduce the effects of the ambient light or bright lights of an operating room during imaging. FIG. 4B is a graph 450 of light intensity as a function of time in accordance with one embodiment of the present invention. The graph 450 includes a pulsed light source's intensity 454 and a room light's intensity 452 over time. As shown, the pulsed light source 454 is turned on (or the light through a selected fiber is switched on) so as to output high intensity light that is significantly brighter than the room intensity 452 during time period 456a and 456b. Otherwise, the pulsed light is off and has zero intensity.

The fluorescent image detection may be timed (or gated) so that fluorescent emissions are only captured during the "on" pulses of the excitation light, while the photographic and/or structured light detection occurs (or gated) during times in which the room light is only present and not the excitation light. As shown, fluorescent detection occurs during time periods 456a and 456b, while photographic and/or structured image detection occurs during time 458.

Illumination during fluorescence capture may include providing light at multiple positions on a different side of the subject as the camera. The ability to select different light sources relative to a fluorescent probe fixed within the subject, provide additional information that is use for 3D tomographic reconstructions. In this case, the excitation light sources are in the form of a plurality of optical fibers that are positioned at different positions on the surgery site's surface or inserted into the surgery site.

In one embodiment, the fluorescent excitation uses a different spectrum than the fluorescent emission. As one of skill in the art will appreciate, the bandgap between excitation and emission filters will vary with the imaging system used to capture the images. A bandgap of at least 25 nm is suitable for many imaging systems. The excitation spectrum may be achieved using any combination of lights and/or filters. The emission spectrum will depend on a number of factors such as the fluorophore used, tissue properties, whether an emission filter is used before the camera, etc. In one embodiment, the location of the excitation light source is moved or different light sources are turned on at different positions to capture multiple images of internal fluorescence and the same set of excitation and emission filters is used for the different excitation light source positions.

A camera then captures a fluorescent light image of at least a portion of the subject (408). The fluorescent image records fluorescence as a function of 2D position. The image may include the entire surgery site, or a portion of interest that has been zoomed in on (optically or digitally). The image is transferred to the image processing unit and/or computer for subsequent processing.

Multiple fluorescent light images may be captured with the current excitation light position (408). In one embodiment, this is done to facilitate spectral unmixing, where each image capture (408) uses a different excitation and/or emission spectrum. In another embodiment, multiple images are taken for differing excitation light source positions. Each illumination position provides a different set of input conditions to the tomographic reconstruction.

All of the images may be used in a tomographic reconstruction, or a subset can be used. The subset may be selected based on a quality measure for the images, such as a threshold for number of fluorescent photons collected in each image. Other quality measures may be used to select the images. The number of images captured may vary. In one embodiment, 1 to about 80 different trans-illumination positions and images are suitable for tomographic reconstruction. In a specific embodiment, from about 4 to about 50 images are suitable. The images may be stored for tomographic assessment at a later time, e.g., the images—or a subset thereof—are recalled from memory during tomographic processing.

In one embodiment, another excitation position is to be used to capture images (412). While the next excitation position is selected, one or more photographic, structured light, and/or fluorescent images of the surgery site may be captured (404 and 406). Image collection may further continue by capturing images of the sample from additional positions. For example, image capture may occur at anywhere from 2 to 200 excitation positions. In general, as more images are captured, more information is gathered for tomographic reconstruction. Also, multiple structured light positions may be used to images more of the surgery site in 3D.

In one embodiment, image capture 204 is automated. A user may initiate software included with an imaging system that controls components of the imaging system responsible for image capture. For example, the user may launch imaging and acquisition software on a computer associated with the imaging system that initializes the camera and carries out imaging automatically. According to stored instructions, the software may then select a desired excitation light position if transillumination is used, prepare the system for photographic, structured light, and/or fluorescent image capture (e.g., turn on/off lights in the excitation lights and gating), focus a lens, selectively position an appropriate excitation or emission filter, select an excitation fluorescent light source (one of many for example), set an f-stop, transfer and store the image data, build a reconstruction, etc. For fluorescent image capture, software activates the camera to detect photons emitted from the surgery site, which usually corresponds to absolute units from the surface. The camera may capture the fluorescent image quickly or over an extended period of time (up to several minutes).

Additional processing may occur on the fluorescent images. Fluorescent imaging often captures image data with multiple reporters; each reporter may have its own wavelength spectrum. A camera image of a surgery site with multiple reporters has the spectral results of each reporter mixed together. In this case, spectral unmixing is useful to clean fluorescent image data and separate the contributions from each source before tomographic processing. The unmixing may also identify contributions from autofluorescence. In one embodiment, a spectral unmixing tool is employed in software to separate fluorescent contributions from multiple sources. This permits fluorescent tomography described herein to image multiple reporters in a surgery site independently. For example, one reporter may be used in an imaging application to monitor cell death in the surgery site, while the second reporter monitors cell propagation. A user may initiate the spectral unmixing tool and software with an appropriate user interface command.

Figure 5:
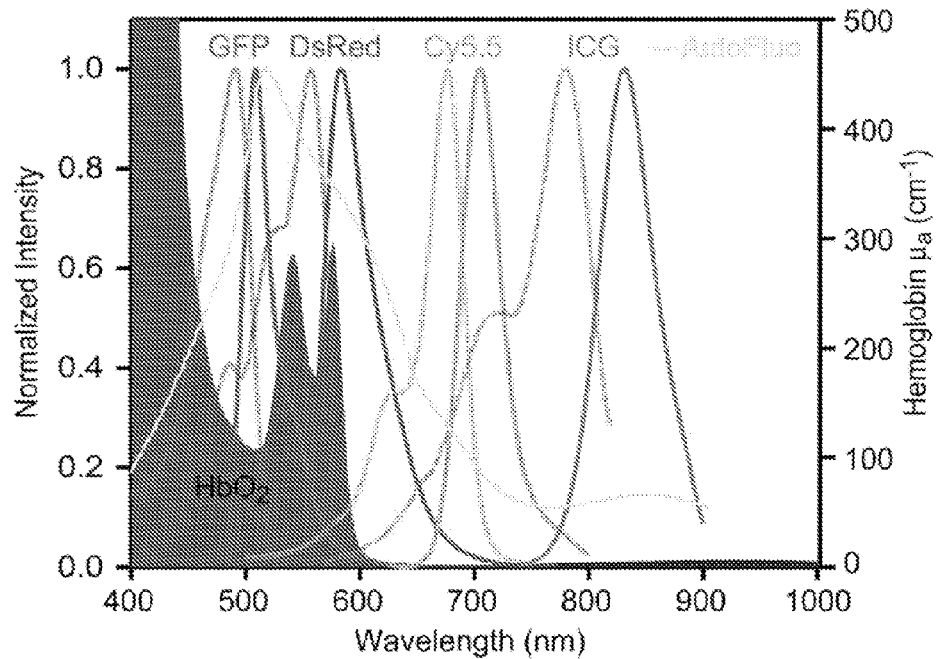
FIG. 5 shows an example of the excitation and emission spectra for multiple types of fluorescence sources.
Figure 6:
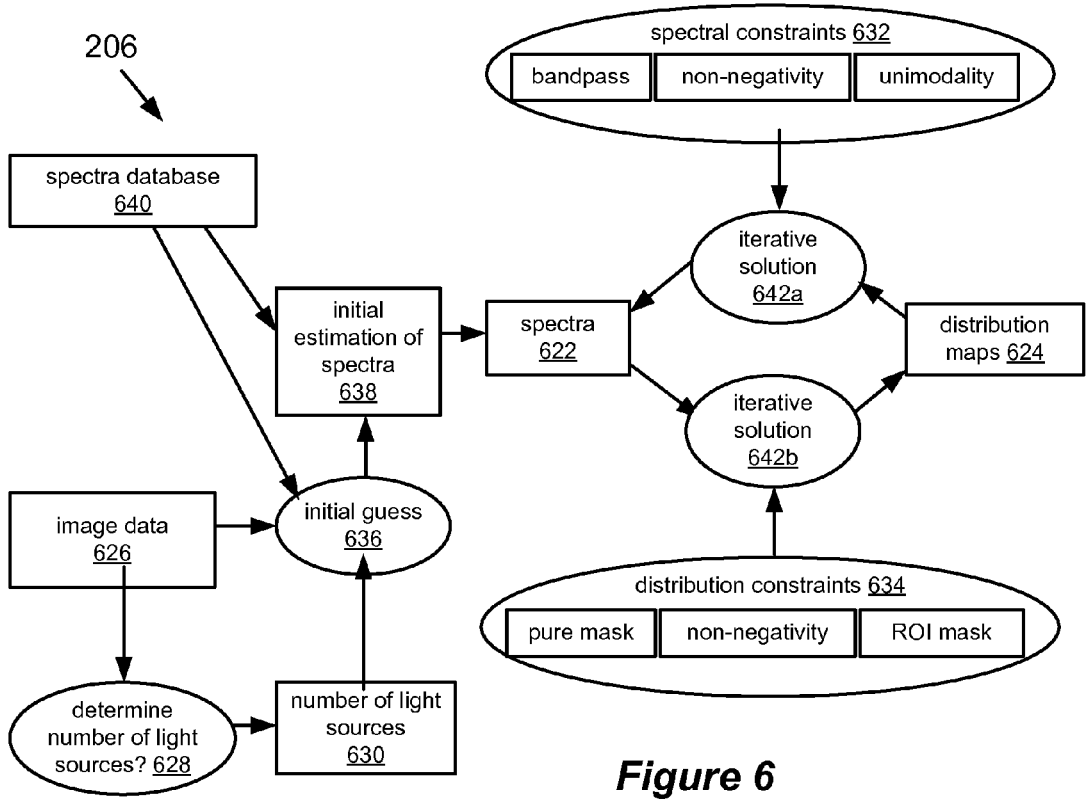
FIG. 6 shows a method for spectral unmixing in accordance with one embodiment.

FIG. 5 shows an example of the excitation and emission spectra for multiple types of fluorescence sources. FIG. 6 shows a method 206 for spectral unmixing in accordance with one embodiment. As mentioned above, the image collection excites a mixture including the light sources at one or more wavelengths, and for each wavelength, collects the emission in a select wavelength range. The output of spectral unmixing method 206 can be a spectrum for one or more light sources and a spatial distribution map for the one or more light sources. As the term is used herein, a spectrum typically refers to a range of light for a light source, often characterized by intensity data for multiple wavelengths in the range. The spectrum may include intensity data for a light source over a wavelength range between about 400 nanometers and about 1300 nanometers. In a specific embodiment, each spectrum is normalized by its peak value and becomes unity at the peak wavelength, while a fraction is assigned to represent the measured signal of the light source at other wavelengths.

The term "spatial distribution map" generally refers to a two-dimensional data representation or other logical distribution of a light source in an image, which usually corresponds to photons emitted from the surface of the surgery area. Isolated spatial distribution maps provide better quantification and localization of light sources and greatly reduce the confusion generated by the autofluorescence in an image. When a peak wavelength is included in the multi-spectral analysis, a distribution map provides a consistent measure of the fluorophore signal regardless how many filters are used to unmix. A spatial distribution map typically bears a limited relationship to the fluorophore spatial distribution map because the fluorescence yield varies with excitation and emission wavelengths and light transportation is affected by the surrounding tissue. While it is possible to correct the quantum yield with a simple calibration, however, this does not account for the light transportation, which is much more challenging and usually requires solving a complex 3D model. Thus, the distribution map should not be regarded as a measure of absolute fluorophore concentration but a tool to compare fluorescence sources at similar imaging conditions and comparable depths.

The input to method 206 shown in FIG. 6 includes an input data matrix, 626, as obtained from one or more fluorescent images. In a specific embodiment, the input data matrix includes fluorescent image data inserted into a matrix comprising the number of samples by the number of wavelengths. The samples refer to pixels in an image, resorted into one-dimension. The wavelengths refer to the excitation and emission wavelength pairs in a data sequence and usually relate to the number of spectral images in a dataset.

Spectral unmixing method 206 first determines how many light sources 130, or components, exist in the data in operation 630. Often, the data only includes two light sources: a fluorescent light source and tissue autofluorescence. However, multiple probes are present in many applications.

In a specific embodiment, spectral unmixing method 206 uses a principal component analysis (PCA) tool on the data matrix 626 to see how many light sources 630 exist in the data. PCA examines variance in the input data 626 as explained by a selected number of principal components. Since principal components are sorted in terms of the variance that they explain, when an additional principal component only affects a small margin of the total explained variance, the previous selected principal components have accounted for the real signals and the rest mainly contribute to random noise.

Principal components are orthogonal to each other, although they do not have biological meanings, they imply the independent real components present in the data. The PCA may also illuminate which wavelengths are important and useful to separate the light sources from other interference signals. For method 206, PCA analysis is implemented as a complimentary tool, but not relied on.

Other approaches can be used to determine the number of underlying light sources (630). Since most in vivo imaging procedures are often set up and users have the knowledge of the fluorophores used, another technique to determine the number of sources 630 lets a user input the number. In addition, if the PCA result is not satisfactory, a user can manually adjust the number and repeat the analysis.

After estimating the number of light sources 630, method 206 determines the size of the problem domain. This is done by multiplying a distribution profile, C, and pure spectra matrix, S. In this case, the distribution profile, C, is a matrix comprising the number of samples (or pixels) by the number of light sources 630, and each column represents the contribution of the corresponding light source, which can be re-interpreted into a 2D distribution map. The pure spectra matrix, S, is a matrix comprising the number of samples light sources 630 by the number of wavelengths, and each row represents the pure component spectrum of this light source. A distribution profile 624 and spectra matrix 622 can also be the output of spectral unmixing method 206.

Method 206 then provides an initial estimation 636 for spectra. Beforehand, the spectral unmixing may classify the data, which helps with an initial guess for iterative processing. Suitable techniques used to classify the data may include Kmean clustering or distance between samples, for example. Other techniques may be used.

When iterative solution process 642 uses MCR and ALS, the iteration is sensitive to the selection of an initial estimate $S_0$ for the spectra in initial guess 636; different initial estimates may lead to different solutions, mainly because there are often multiple local minimums in a solution space for such a high degree of freedom problem. There are several approaches to find a suitable initial estimate 636. The initial estimation 636 may use: the input data 626 and a clustering method, a random sampling, and/or an a priori spectra database 640 that includes historical initial estimates that have worked well. Another systematic initial estimate uses an evolving factor analysis (EFA) and SIMPLISMA to extract the pure component spectra. To make the initial estimate close to the true solution and stable, another approach uses a statistical data analysis and k-means clustering method. This partitions the dataset 626 into k groups on a measure of distance between samples; the centroids of these groups are used as the initial estimate. The distance measure determines how the similarity of two samples is calculated. A correlation distance measure may be chosen because it emphasizes the spectrum shape and is not affected by the scaling due to the contribution. Alternatively, an initial estimate $S_0$ for the spectra can be loaded from an a priori spectra library, or from a spectra in a user selected region of interest (ROI) of the image. This latter option gives the user more control to the unmixing algorithm, which is useful for in vitro imaging where pure components are relatively easy to determine and pure spectra do not change significantly. The initial estimate may also be fixed when: all the spectra are fixed, the iterative alternating least squares (ALS) degenerates to single step least squares, and thus method 206 is simplified to a popular linear unmixing algorithm in fluorescence microscopy. The initial estimation 636 produces an initial spectra estimate $S_0$ 638.

Method 66 then uses an iterative process (642) that solves the problem C*S=D where C and S are both unknown. It is an under-determined system and infinite solutions exist. One suitable output is then a best approximate solution of the linear system given one or more constraints. In one embodiment, an iterative solver is used. The iterative solver may use any conventional finishing criteria, such as a least squares error approximation.

In one embodiment, method 206 uses multivariate curve resolution (MCR) and alternating least squares techniques (ALS) to produce the output spectra 622 and spatial distribution map 624 for a contributing light source. In a specific embodiment, iterative solution process 642 solves for two alternating least-square problems: loop 142a) minimizing of C*S=D over S for given C; and loop 642b) minimization of C*S=D over C for given S. This technique neither relies on pre-measured in vitro spectra of light sources nor requires manually selection of pure components. Similar to principal component analysis (PCA), MCR explains the data variance with some principal components, but, differently, it finds realistic components instead of mathematical ones. With input of multi-spectral images 626 and a few constraints 632 and 634, the unmixing method 206 automatically outputs the pure spectra 622 and a spatial distribution map 624 of each internal light source.

To help converge to a unique and realistic solution, method 206 adds one or more constraints 632 and 634 to the iteration process. Constraints 632 and 634 may come from knowledge about the variables, such as non-negativity. The constraints reduce the solution space by enforcing some boundaries and help solve the rotation ambiguity inherent in a bilinear model. Here, the rotation ambiguity refers to the fact that any arbitrary k by k orthogonal matrix $Q$ ($Q^TQ=I$, I is identity matrix) can result another suitable solution $CQ^T$ and QS for the bilinear model. A special case of the rotation ambiguity that Q is a diagonal matrix is often known as the scaling ambiguity. Usually this cannot be solved by setting the constraints and thus a normalization procedure may be enforced on either C or S throughout the iteration. The convergence is achieved when the absolute change of a residual norm $e^2$ or some other error assessment passes below a threshold (e.g., 0.1% error). After convergence, method 66 outputs matrices for C and S, which represent the output spectra 622 and spatial distribution maps 624, respectively.

Thus, as an underdetermined system, output improves as spectral unmixing method 206 knows more about the data. In general, the constraints 632 and 634 may include any limit on the modeling and solution-space. In one embodiment, the constraint limits internal light modeling by one or more practical considerations.

In one embodiment, the constraint includes a spectral limit 632. One suitable spectral constraint is non-negativity that limits both spectra and distributions to non-negative numbers. Non-negativity constraints are applied after each calculation for S or C using least squares method $S=(C^TC)^{-1}C^TD$ or $C^T=(SS^T)^{-1}SD^T$. Instead of setting negative elements to zero, a more rigorous method non-negative least squares (NNLS) is used to recalculate the solution at the columns of S or the rows of C where comprise negative elements rather than the whole matrix.

A unimodality spectral constraint 632 limits the spectrum for each light source to a single peak, which has a monotonic and smoothing effect. Unimodality constraints are suitable for fluorescence spectra since fluorophores usually only have single excitation or emission peak. Typically, a user has a priori knowledge about the fluorescent light sources, such as input spectra for the fluorescent reporters stored in a database 140. For automated spectral unmixing, fluorophore(s) used in the fluorescent probe are typically known for an imaging application, and optical properties for the fluorophore wavelengths are also known and stored in software. Other known fluorophore properties may include excitation wavelength band and extinction coefficient and quantum efficiency, for example.

Another spectral constraint 632 uses a bandpass constraint, which limits the spectral data input to the iterative solution process to within a desired wavelength range. In a specific embodiment, the bandpass constraint relates to a known fluorophore used in the animal. The emission wavelength band of most fluorophores has a sharp increase from a shorter wavelength range to its emission peak, after which it decreases relatively slowly towards longer wavelengths. If the fluorophore is known, a high pass filter may be used to suppress the unwanted spectrum below its rising edge. Similarly, for most fluorescent dyes, low pass filter can be used when solving for excitation wavelength band to eliminate higher wavelength values.

Bandpass constraint information may also come from the filter combination used in image capture. A predetermined wavelength range for a wavelength filter used in image capture (and the spectrum properties for the fluorophore at that wavelength range) may then be input to iterative solution 642.

In a specific embodiment, the imaging process is automated and a computer recalls spectrum constraints 632 for the filter and fluorophore from memory. A graphical user interface associated with the imaging system allows a user to select one or more fluorophores or filters from a list, where information for each fluorophore and filter is stored in a database.

In another embodiment, the constraint is applied to the spatial light distribution map 634. For example, an image or equality constraint may also be applied, which limits the light values within explicit spatial boundaries of the spatial distribution map. This may include: a spatial image limit (e.g., the region of pure component samples that can be selected), a region of interest analysis that defines a 2D spatial image limit in the image, a pass band for an individual spectrum, etc. A pure mask constraint 134, assigned to a light source, determines an image region that only contains a particular light source. In other words, the contribution of other light sources in this mask is zero. An ROI mask associated with a component determines a region in the image that this component might exist, in other words, outside of this mask the contribution of a component is zero.

Method 206 also applies the selected spatial distribution map constraints 634 to the intended light source 630. For example, assuming there are two components, one is the tissue autofluorescence with a broad spectrum and the other is a red fluorescent dye with a sharp spectrum, method 206 ensures that an ROI constraint is applied to the dye not autofluorescence. This stems a component-wise rotation ambiguity and crisis regarding mismatch between the initial estimate and its constraints. To disentangle such ambiguity, spectra are automatically sorted in each iteration 642 in ascending order of their center wavelengths (power weighed average), i.e., by the color of the fluorophores. In this example, the red fluorescent dye is tagged next to a yellowish autofluorescence and the user or software can easily apply constraints.

Figure 7:
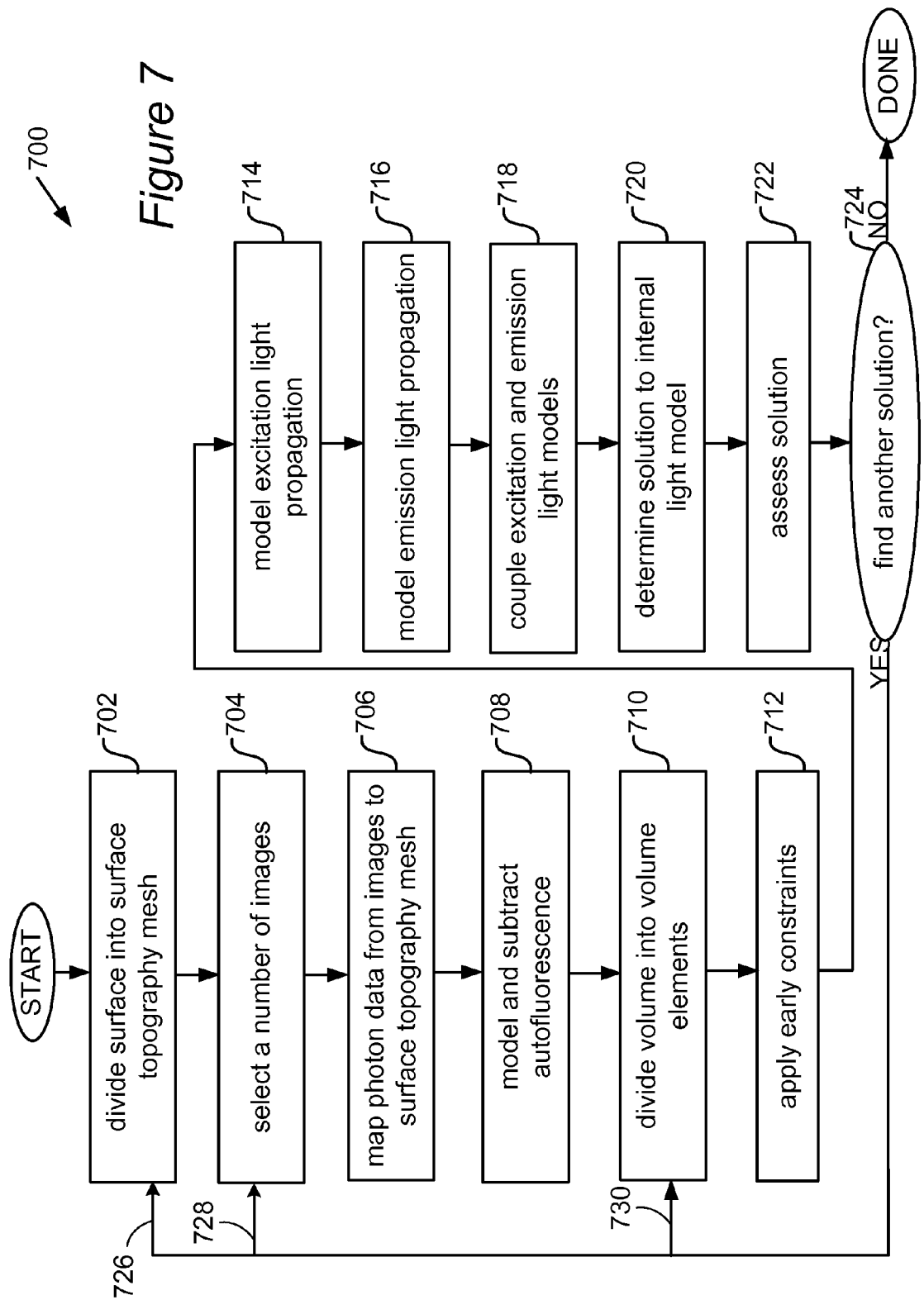
FIG. 7 shows a process flow 700 for obtaining a 3D representation of a fluorescent probe distribution located inside surgery site in accordance with a specific embodiment of the present invention.

FIG. 7 shows a process flow 700 for obtaining a 3D representation of a fluorescent probe distribution located inside surgery site in accordance with a specific embodiment of the present invention. Process flow 700 expands upon method 200 of FIG. 2, and converts surface light emission data to a mathematical representation of a fluorescent probe distribution within the surgery site.

Process flow 700 first divides a surface representation for the surgery site into a surface mesh that includes a set of surface elements (702). This process may include obtaining a surface topography, if that has not already been done (see 208 in FIG. 2). The number of surface elements will vary according to the surgery site's surface area and the desired solution accuracy for the tomographic reconstruction. The number of surface elements in the set should be large enough to capture photon density details and variation across the object of interested of the surgery site surface. For example, between about 100 and about 10,000 surface elements may be suitable for a surgery site.

Process flow 700 may then include selection of a number of images for use in the tomographic assessment (704). As mentioned above in image capture, not all images previously captured and stored in memory need be used. For example, a user may select images that include different trans-illumination light source positions that are closer to a fluorescent probe, as compared to other images where the trans-illumination light source position is farther away from the probe. Epi-illumination images may also be incorporated into process flow 700.

Process flow 700 may include mapping photon data from the images to the surface topography mesh (706). This operation may include the mapping techniques described above in 208 of FIG. 2.

Expanding upon the mapping described above with respect to 208 in FIG. 2, the mapping may include converting surface light data (excitation and/or emission) into light data internal to a surface. Notably, this relates surface emission intensity to photon density just inside the surgery site surface. In one embodiment, process flow 700 converts values of light emission intensity for each surface element into photon density just inside the surface. Referring briefly to FIG. 3C, the value of emission intensity at a surface element, $I(\theta_2)$, is related to the photon density $\rho$ beneath the surface element. The exact form of the relationship depends on the model used to describe the transport of photons across the surface boundary. One embodiment of this relationship, based on the partial-current boundary condition, is given by:

$$I(\theta_2) = \frac{c}{4\pi n^2} T(\theta)\cos\theta_2 d\Omega \left[1 + \frac{3}{2}\frac{1-R_{\text{eff}}}{1+R_{\text{eff}}}\cos\theta\right]\rho \quad (1)$$

Here, c is the speed of light, n is the index of refraction of the sample medium, T is the transmission coefficient for light exiting the sample through the surface element, and $\theta$ is the internal emission angle, which is related to the external emission angle $\theta_2$ through Snell's law:

$$n \sin \theta = \sin \theta_2 \quad (2)$$

The parameter $R_{\text{eff}}$ is the average internal reflection coefficient calculated from the following formulae:

$$R_{\text{eff}} = \frac{R_\phi + R_j}{2 - R_\phi + R_j} \quad (3)$$

$$R_\phi = \int_0^{\pi/2} 2\sin\theta\cos\theta R(\theta) d\theta$$

$$R_j = \int_0^{\pi/2} 3\sin\theta\cos^2\theta R(\theta) d\theta$$

-continued $$R(\theta) = \begin{cases} \frac{1}{2}\left(\frac{n\cos\theta_2 - \cos\theta}{n\cos\theta_2 + \cos\theta}\right)^2 + \frac{1}{2}\left(\frac{n\cos\theta - \cos\theta_2}{n\cos\theta + \cos\theta_2}\right)^2 & \text{for } \theta < \arcsin(1/n) \\ 1 & \text{for } \theta > \arcsin(1/n) \end{cases}$$

Thus, the internal reflectivity $R_{\text{eff}}$ depends on the index of refraction of the medium underneath a surface element. In tissue for example, $R_{\text{eff}}$ is typically in the range of 0.3-0.5.

Eqs. (1) and (2) may thus be used to convert surface emission data measured at each surface element to values of the photon density beneath the surface.

Autofluorescence is then unmixed (or modeled and subtracted) from the surface emission data (708). Suitable techniques for doing so were described above with respect to 208 in FIG. 2.

Referring back to FIG. 7, process flow 700 may then include dividing the surgery site interior volume into volume elements, or 'voxels' (710). One or more early constraints may also be applied (712) to expedite or simplify the determination, such as applying one or more limits on the modeling and solution-space. In one embodiment, the internal light modeling solution space is spatially limited to within the boundaries of the surgery site surface. In another embodiment, a volume space used within the reconstruction is limited by one or more practical considerations. For example, regions of the internal surgery site volume far away from where fluorescent light emission takes place, as determined by a visual scan of the images, may be excluded from the solution space.

Process flow 700 may then include modeling light propagation. In the embodiment shown, this modeling may occur in a three-step process where excitation light and emission light are each modeled separately and then the two are combined (714, 716, and 718).

Light transport in turbid media such as tissue is dominated by scattering and is substantially diffusive in nature. In one embodiment, tissue scattering and absorption parameters are known a priori, stored in memory, and recalled from memory when a reconstruction occurs.

In many instances, the condition for diffusive transport is that the scattering coefficient $\mu_s$ be greater than the absorption coefficient $\mu_a$ so that the change in the photon density is small between scattering events. The photon density produced by a source power density, $U_i$, in a homogeneous medium may be represented by the diffusion equation:

$$D\nabla^2\rho - \mu_a c\rho = -U_i(\underline{x}) \quad (4)$$

where the diffusion coefficient D is, $$D = \frac{c}{3(\mu_A + \mu_S')} \quad (5)$$

An emission Green's function is a solution to Eq. (9) subject to the boundary condition imposed by the surface of the sample.

In a specific embodiment, a Green's functions is used to model internal light propagation. A Green's function mathematically describes light propagation through space, such as through tissue, from one location to another. In one embodiment, the Green's function uses volume elements and surface mesh elements as vector spaces for its data elements. In a specific embodiment, an excitation Green's matrix models light propagation from a position of the excitation illumination source to the volume elements (714). An emission Green's matrix may also be used to model light propagation from the volume elements to the surface elements (716).

The excitation and emission models are then combined (718). In a specific embodiment, the excitation and emission Green's function matrices are coupled together, along with a coupling constant, and form a single fluorescence Green's kernel matrix for the fluorescence forward model. In another specific embodiment, the excitation Green's function and emission Green's function matrices are composed using a hybrid Green's function expression which combines weighted terms of a radial partial current boundary condition and an extrapolated boundary condition. This coupled Green's function may be applied to fluorescence of the probe and/or autofluoresence.

Other modeling processing and factors are suitable for use. Modeling may also include one or more of the following operations: a) establishing a relationship between the surface elements and volume elements, b) setting additional limits on the modeling and solution-space, c) deciding whether to use a homogeneous or non-homogeneous model for light propagation in tissue, and/or d) composing a mathematical representation of light internal to the surgery site.

Referring back to FIG. 7, process flow 700 may then include determining the light data internal to the surgery site, including the desired fluorescent probe distribution that includes the fluorescent probe (720). For example, once the Green's function is determined, the distribution may be obtained by solving the system of linear equations that relate the photon density at the surface to the source distribution inside the object. In one embodiment, process flow 700 solves for all the internal volume elements. Thus, once the Green's function is modeled and determined, it may be evaluated for every volume element—surface element pair, in order to obtain the system of linear equations (Eq. 7, below). Referring forward to Eq. (7), since $\rho$ is known, and $G_{ij}$ can be determined as described below, the reconstruction method then solves the linear system, Eq. (7), for the source strengths $S_i$.

Typically, there is no exact solution to the linear system because the collection of point sources is only an approximation of the actual source distribution. One suitable reconstruction is then the best approximate solution of the linear system. In a specific embodiment, process flow 700 uses the non-negative least squares algorithm to solve for the internal fluorescent probe distribution. Other techniques may be used. In some cases where the fluorescent probe distribution includes a spatially smoother solution, Eq. (7) can be augmented using a regularizing matrix in the first derivative.

In one embodiment, the present invention relies on a simplified analytical approximation (planar boundary condition) for the Green's function. In another embodiment, a look-up table can be used for the Green's function. The look-up table may be created by previous measurements of photon transport in a sample (or similar sample approximated to be substantially equal to the current sample), or by computational simulations using techniques such as Monte Carlo or finite element modeling. This particular method is useful for samples consisting of inhomogeneous media, such as animal or human subjects. In this case, the optical properties of the tissue, $\mu_a$ and $\mu_s$ may have spatial dependence or other heterogeneous properties.

In one embodiment, process flow 700 applies an iterative solution process. Iterative processing obtains multiple three-dimensional representations and compares them to improve the final output and assessment for the fluorescent probe distribution. In this case, process flow 700 includes varying the tomographic assessment or modeling, finding a potentially new of different solution in each iteration, and then selecting one of the multiple solutions. Loop 728, for example, varies the subset of images that were selected from a larger set of images.

To facilitate comparison between iterations, iterative process flow assesses the solution quality and assigns a quality to each iterative solution (722). In one embodiment, the assessment measures a difference between the observed photon density and the calculated photon density. For example, a "chi squared" criteria may be used:

$$\chi^2 = \sum_i \left[ \frac{\rho_i - \sum_j G_{ij}s_j}{\rho_i} \right]^2 \qquad (6)$$

The value of $\chi^2$ measures the difference between the observed photon density $\rho_i$ and the calculated photon density $$\sum_j G_{ij}s_j$$

over the surface of the sample. Other terms shows in Equation 6 are described further below with respect to Equations 7-9.

In one embodiment, iterative process flow includes varying volume element configuration. Loop 730 varies the number and/or size of volume elements. In this case, volume element size is initially set, and changed as iteration proceeds. In some cases, the initial voxelation is relatively coarse and refined with successive iterations. For example, the volume element size may be reduced by a factor of two in a next iteration. If the solution quality improves after this second pass, then the volume element size may be again reduced by a factor of two in a third iteration. If the solution quality doesn't improve or gets worse, then the algorithm may have converged on a final solution and stop. In one embodiment, the initial volume element size may range from about 0.1 mm³ to about 1 cm³, and subsequent and/or final volume element size for volume elements close to the source may reduce from about 1 mm³ to about 10 mm³. In a specific example, the initial volume element size may be about 200 mm³ or about 1 cm³, and the final volume element size for volume elements close to the source may reduce to about 1 mm³.

In some cases, it is advantageous to reduce the number of volume elements in the problem while maintaining a high density of volume elements in the vicinity of the fluorescent probe. This reduction can be achieved by using adaptive meshing. In one embodiment, adaptive meshing increases the density of the solid mesh near the probe to provide increased volumetric information in this space, while density of the solid mesh decreases in areas where no activity of interest is taking place (no light generation or transport). In one suitable adaptive meshing application, a coarse volume element mesh is initially applied throughout the entire sample volume and the current solution is found, yielding an initial solution for $S_j$. Next the volume elements that have source strengths greater than zero ($S_j$>0) are refined (i.e. subdivided) and those where the source strengths equal zero ($S_j$=0) are removed. Solution attainment and volume element mesh refinement may then be iterated repeatedly, producing a high-density volume element mesh localized around the fluorescent probe distribution. For each iteration loop, the quality of the current solution is assessed (722). In a specific embodiment, the iteration continues until further refinement produces no significant decrease in the assessment value.

An additional iterative improvement may be obtained by varying the number of surface elements, $N_S$, used in obtaining the three-dimensional representation (loop 726). Using a subset of the surface elements of the surface mesh reduces the number of constraints in the problem, which may simplify and expedite solution calculation. The number of surface elements may be used to sample the surface uniformly. In this case, process flow 700 iterates for different values of $N_S$ corresponding to sampling the surface element mesh at different densities, and use the quality assessment (722) to determine the best solution among the different values of $N_S$. For example, if the number of surface elements is between about 100 and about 700 surface elements for a small surgery site, an iteration step size between about 10 and 50 may be suitable.

Figure 8:
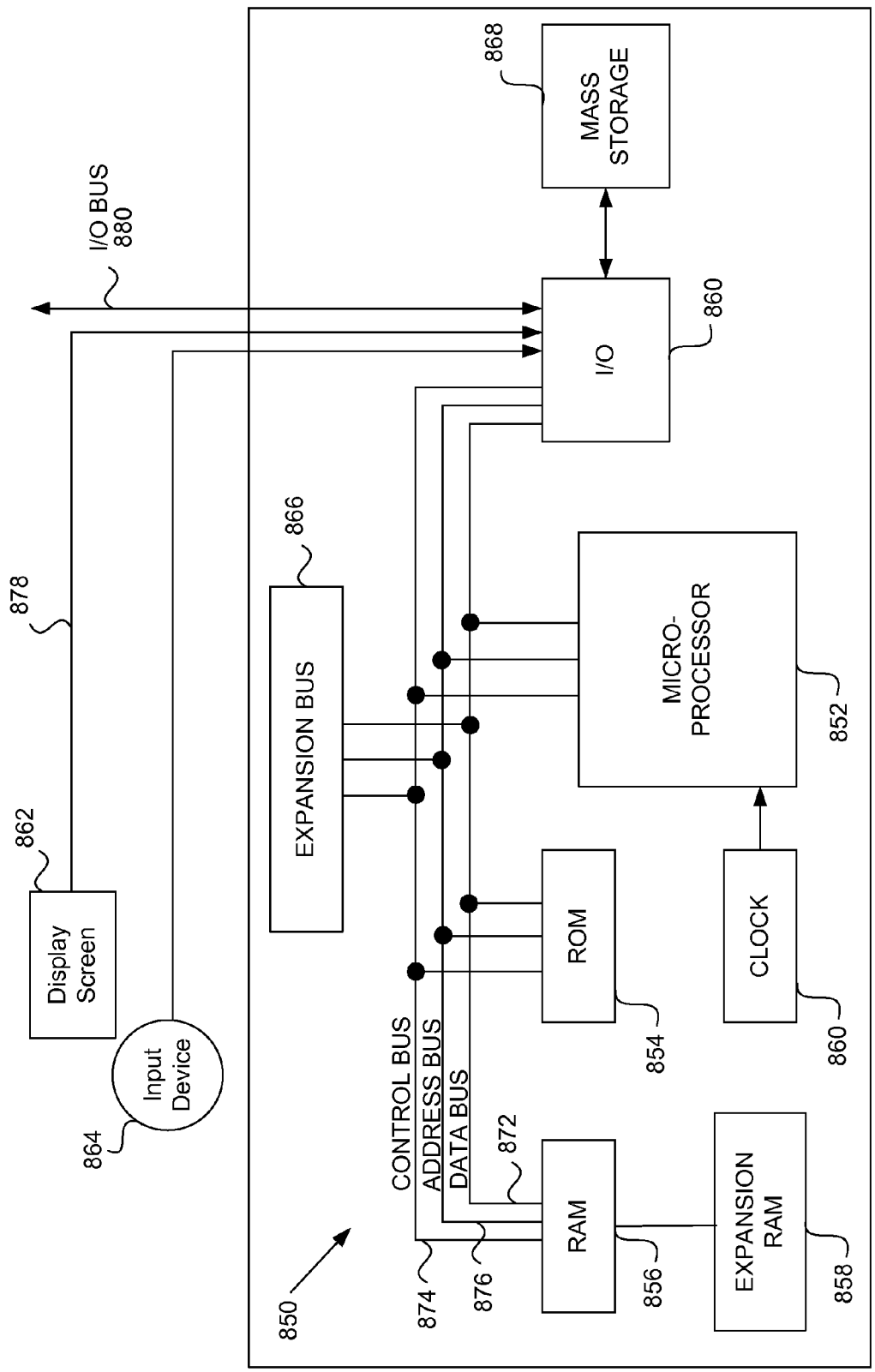
FIG. 8 is a diagrammatic representation of an exemplary computer system for implementing techniques of the present invention.

The imaging and analysis techniques of the present invention will typically be managed by a suitable processor or computer-based apparatus, e.g., the processor and controller 120 or electronic gate control 110 of FIG. 1. Referring to FIG. 8, an exemplary computer system 850 may include a central processing unit (CPU) 852, read only memory (ROM) 854, random access memory (RAM) 856, expansion RAM 858, input/output (I/O) circuitry 860, display assembly 862, input device 864, and expansion bus 866. Computer system 850 may also optionally include a mass storage unit 868 such as a disk drive unit or nonvolatile memory such as flash memory and a real-time clock 860.

Regardless of the particular configuration for computer system 850, it may employ one or more memories or memory modules configured to store program instructions for fluorescent imaging and obtaining a three-dimensional representation of a light source located inside a subject and other functions of the present invention described herein. Such memory or memories may also be configured to store data structures, imaging data, or other specific non-program information described herein.

Because such information and program instructions may be employed to implement the systems/methods described herein, the present invention relates to machine-readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). The invention may also be embodied in a carrier wave traveling over an appropriate medium such as airwaves, optical lines, electric lines, etc. Examples of program instructions include both machine code, such as produced by a compiler, and files containing higher level code that may be executed by the computer using an interpreter.

It should be borne in mind that although computer system 850 is discussed in some detail herein to facilitate discussion, the invention may be practiced using a variety of suitable computer-implemented techniques. In general, any suitable computer system may be employed for imaging and obtaining a three-dimensional representation of a light source located inside a sample. Further, the inventive reconstruction techniques disclosed herein may be implemented via a computer network, such as a local area network (LAN), wide area network (WAN) or a global computer network such as the Internet. In the latter cases, the imaging and reconstruction techniques may be implemented at least in part as downloadable computer software and data (e.g., applets such as JAVA™ applets from Sun Microsystems Inc.). The downloadable computer software and data may be kept on one or more servers on the network, accessible by any client computer or terminal capable and authorized for such access. Network computing techniques and implementations are well known in the art and are not discussed in great detail here for brevity's sake.

Although the foregoing invention has been described in some detail for purposes of clarity of understanding, it will be apparent that certain changes and modifications may be practiced within the scope of the appended claims. Therefore, the present embodiments are to be considered as illustrative and not restrictive and the invention is not to be limited to the details given herein, but may be modified within the scope and equivalents of the appended claims.

What is claimed is:

1. A method of determining a distribution of fluorescence emission sources in patient in an operating room, the method comprising:
    illuminating a surgery site of the patient through a hollow inner portion of a support member with structured illumination light, and obtaining an image of the structured illumination light on the surgery site;
    illuminating the surgery site at a plurality of different positions by sequentially directing excitation light through different optical fibers, wherein each one of the optical fibers extends through a solid outer portion of the support member, and obtaining a plurality of images of fluorescence emission from the surgery site, wherein each one of the plurality of fluorescence emission images corresponds to illumination through a different one of the optical fibers;
    determining a three-dimensional surface representation of at least a portion of the surgery site based on the image of the structured illumination light on the surgery site;
    determining a distribution of fluorescence emission in a boundary region inside a surface of the surgery site based on the plurality of images of fluorescence emission and the three-dimensional surface representation; and
    determining a distribution of fluorescence emission sources internal to the surgery site based on the distribution of fluorescence emission in the boundary region by performing a tomographic reconstruction based on a photon diffusion model.

2. The method of claim 1, further comprising illuminating the surgery site with pulsed excitation light, and synchronizing the obtaining of the plurality of fluorescence emission images with the pulsed excitation light.

3. The method of claim 1, further comprising:
    overlaying an image of the distribution of fluorescence emission sources internal to the surgery site with the three-dimensional surface representation to form an overlay image; and
    displaying the overlay image on a display unit.

4. The method of claim 1, wherein each of the plurality of different illumination positions is on a first side of the surgery site, the method further comprising obtaining each one of the plurality of fluorescence emission images on a second side of the surgery site different from the first side.

5. The method of claim 1, wherein each of the plurality of different illumination positions is on a common side of the surgery site, the method further comprising obtaining each one of the plurality of fluorescence emission images from the common side of the surgery site.

6. The method of claim 1, further comprising:
unmixing spectral contributions from autofluorescence to the plurality of fluorescence emission images prior to determining the distribution of fluorescence emission sources internal to the surgery site.

7. The method of claim 1, further comprising unmixing spectral contributions from operating room lights to the plurality of fluorescence emission images prior to determining the distribution of fluorescence emission sources internal to the surgery site.

8. The method of claim 1, further comprising determining the distribution of fluorescence emission sources internal to the surgery site in a period of 1 minute or less.

9. The method of claim 1, further comprising subtracting autofluorescence spectral contributions from the plurality of fluorescence emission images prior to determining the distribution of fluorescence emission in the boundary region.

10. An imaging apparatus for determining a distribution of fluorescence emission sources in a patient in an operating room, the apparatus comprising:
a support member comprising an outer solid portion and a hollow interior portion;
a plurality of optical fibers, wherein the excitation light that extend through the outer solid portion of the support member;
one or more excitation light sources configured to provide excitation light at a surgery site of the patient by directing the excitation light through the plurality of optical fibers;
a structured light source configured to generate structured illumination light;
a photographic imager for obtaining one or more images of the surgery site;
a fluorescence imager for detecting fluorescent emission from the surgery site in response to the excitation light; and
a controller configured to:
activate the structured light source to illuminate the surgery site through the hollow portion of the support member with structured illumination light, and to obtain an image of the structured illumination light on the surgery site using the photographic imager;
activate the one or more excitation light sources to sequentially direct the excitation light through each one of the plurality of optical fibers in turn to illuminate a different position at the surgery site, and to obtain a plurality of images of fluorescence emission from the surgery site using the fluorescence imager, wherein each one of the plurality of fluorescence emission images corresponds to illumination through a different one of the optical fibers;
determine a three-dimensional surface representation of at least a portion of the surgery site based on the image of the structured illumination on the surgery site;
determine a distribution of fluorescence emission in a boundary region inside a surface of the surgery site based on the plurality of images of fluorescence emission and the three-dimensional surface representation; and
determine a distribution of fluorescence emission sources internal to the surgery site based on the distribution of fluorescence emission in the boundary region by performing a tomographic reconstruction based on a photon diffusion model.

11. The imaging apparatus of claim 10, wherein the controller is configured to synchronize the obtaining of the plurality of fluorescence emission images with pulsed activation of the one or more excitation light sources.

12. The imaging apparatus of claim 10, wherein the controller is configured to:
overlay an image of the distribution of fluorescence emission sources internal to the surgery site with the three-dimensional surface representation to form an overlay image; and
display the overlay image on a display unit.

13. The imaging apparatus of claim 10, wherein the one or more excitation light sources sequentially direct the excitation light to illuminate different positions on a first side of the surgery site, and wherein the controller is configured to obtain the plurality of fluorescence emission images from a second side of the surgery site different from the first side.

14. The imaging apparatus of claim 10, wherein the one or more excitation light sources sequentially direct the excitation light to illuminate different positions on a common side of the surgery site, and wherein the controller is configured to obtain the plurality of fluorescence emission images from the common side of the surgery site.

15. The imaging apparatus of claim 10, wherein the controller is configured to unmix spectral contributions from autofluorescence to the plurality of fluorescence emission images prior to determining the distribution of fluorescence emission sources internal to the surgery site.

16. The imaging apparatus of claim 10, wherein the controller is configured to unmix spectral contributions from operating room lights to the plurality of fluorescence emission images prior to determining the distribution of fluorescence emission sources internal to the surgery site.

17. The imaging apparatus of claim 10, wherein the one or more excitation light sources are movable, and wherein the controller is configured to:
activate one of the one or more excitation light sources;
sequentially translate the activated excitation light source so that each one of the optical fibers is coupled in turn to the activated light source to sequentially illuminate the different positions at the surgery site.

18. The imaging apparatus of claim 10, wherein the controller is configured to determine the distribution of fluorescence emission sources internal to the surgery site in a period of 1 minute or less.

19. The imaging apparatus of claim 10, wherein the controller is configured to subtract autofluorescence spectral contributions from the plurality of fluorescence emission images prior to determining the distribution of fluorescence emission in the boundary region.

20. The imaging apparatus of claim 10, wherein the support member is a ring.

21. The imaging apparatus of claim 10, wherein the support member has a cross-sectional shape in a form of at least one of a triangle, an oval, a square, a rectangle, and a polygon.

* * * * *

UNITED STATES PATENT AND TRADEMARK OFFICE
CERTIFICATE OF CORRECTION

| | |
|---|---|
| PATENT NO. | : 9,080,977 B2 |
| APPLICATION NO. | : 11/877414 |
| DATED | : July 14, 2015 |
| INVENTOR(S) | : Pamela Reilly Contag and Bradley W. Rice |

It is certified that error appears in the above-identified patent and that said Letters Patent is hereby corrected as shown below:

In the Specification

Column 1

Line 7 (Approx.), Delete "119(e)" and insert -- §119(e) --

Signed and Sealed this
Twenty-second Day of December, 2015

Michelle K. Lee
*Director of the United States Patent and Trademark Office*